(12) United States Patent
Montero et al.

(10) Patent No.: US 11,844,728 B1
(45) Date of Patent: Dec. 19, 2023

(54) METHOD AND APPARATUS FOR A FLAT, SINGLE PIECE, FOLDABLE, COMPLETE, MEDICAL FACE SHIELD

(71) Applicants: Frank J. Montero, Windermere, FL (US); Anned Montero, Windermere, FL (US)

(72) Inventors: Frank J. Montero, Windermere, FL (US); Anned Montero, Windermere, FL (US)

( * ) Notice: Subject to any disclaimer, the term of this patent is extended or adjusted under 35 U.S.C. 154(b) by 0 days.

(21) Appl. No.: 17/214,752

(22) Filed: Mar. 30, 2021

(51) Int. Cl.
*A61F 9/02* (2006.01)
*A41D 13/11* (2006.01)

(52) U.S. Cl.
CPC .......... *A61F 9/029* (2013.01); *A41D 13/1161* (2013.01); *A41D 13/1184* (2013.01); *A61F 9/027* (2013.01)

(58) Field of Classification Search
CPC ................ A41D 13/11; A41D 13/1107; A41D 13/1161; A41D 13/1184; A41D 13/1192; A42B 1/208; A42B 1/0192; Y10T 24/1498; Y10T 24/153; Y10T 24/141
See application file for complete search history.

(56) References Cited

U.S. PATENT DOCUMENTS

| | | | |
|---|---|---|---|
| 2,961,785 A * | 11/1960 | Toepfer | G09F 3/04 24/DIG. 43 |
| 4,825,878 A | 5/1989 | Kuntz et al. | |
| 4,852,186 A * | 8/1989 | Landis | A41D 13/1184 2/9 |
| 4,867,178 A * | 9/1989 | Smith | A41D 13/1184 2/9 |
| 4,920,576 A * | 5/1990 | Landis | A41D 13/1184 2/9 |
| 4,944,294 A | 7/1990 | Borek, Jr. | |
| 5,010,590 A * | 4/1991 | Haber | A42B 1/208 2/209.3 |
| 5,113,528 A | 5/1992 | Burke, Jr. et al. | |
| 5,150,703 A | 9/1992 | Hubbard et al. | |
| 5,341,513 A * | 8/1994 | Klein | A61F 9/02 128/857 |
| 5,440,760 A | 8/1995 | Highsmith | |
| 5,446,925 A | 9/1995 | Baker et al. | |

(Continued)

FOREIGN PATENT DOCUMENTS

| | | | | |
|---|---|---|---|---|
| DE | 202020102103 U1 * | 5/2020 | | |
| DE | 202020102176 U1 * | 6/2020 | | |
| WO | WO-2013054283 A1 * | 4/2013 | ............. | A61F 9/029 |

*Primary Examiner* — F Griffin Hall

(57) ABSTRACT

The present invention relates to a light-weight, self-contained, one piece, ventilated, washable, disposable, face shield for the protection of regions penetrable membranes, such as the eyes, nose and mouth of medical personnel, essential workers and the general public from exposure to infectious, and/or hazardous pathogens carrying fluids and particulate materials such as the Coronaviridae family of viruses including COVID-19. Some embodiments include a front facing transparent face plate, a plurality of adjustable flaps to customize the angle of protection, a mechanism to separate the transparent front facing face plate from the user's forehead, an attaching and sizing mechanism to conform to the user's head. Some embodiments may use materials that inherently, or through the application of special coatings, provide additional optical protections.

18 Claims, 22 Drawing Sheets

Origami One Piece X-Face Shield Components - Flat Position - Orthographic View

Origami One Piece X-Face Shield Fourth Fold - Perspective View

(56) References Cited

U.S. PATENT DOCUMENTS

| | | | |
|---|---|---|---|
| D375,583 S | 11/1996 | Landis et al. | |
| 5,584,078 A | 12/1996 | Saboory | |
| 5,647,060 A | 7/1997 | Lee | |
| 5,692,522 A | 12/1997 | Landis | |
| 5,732,410 A | 3/1998 | Machson | |
| 5,983,390 A | 11/1999 | Desy | |
| 6,016,808 A | 1/2000 | Landis | |
| 7,540,039 B2 | 6/2009 | Reaux | |
| 8,261,375 B1 | 9/2012 | Reaux | |
| 9,949,517 B2 | 4/2018 | Howard | |
| D899,002 S * | 10/2020 | Chapman | A41D 13/1184 D29/110 |
| D910,241 S * | 2/2021 | Koefelda | D29/110 |
| D920,584 S * | 5/2021 | Weber | D29/110 |
| D925,834 S * | 7/2021 | Babin | D29/110 |
| D933,904 S * | 10/2021 | Weber | D29/110 |
| 11,206,881 B2 * | 12/2021 | Sprouse | A41D 13/1161 |
| 2006/0143766 A1 | 7/2006 | Ramsey | |
| 2008/0010726 A1 | 1/2008 | Vincent et al. | |
| 2010/0146679 A1 | 6/2010 | Heil | |
| 2021/0298390 A1 * | 9/2021 | Sup, IV | A41D 13/1184 |
| 2021/0307426 A1 * | 10/2021 | Block | A41D 13/1184 |
| 2021/0307446 A1 * | 10/2021 | Baz | A42B 3/20 |
| 2021/0329999 A1 * | 10/2021 | Ackerman | A41D 13/1161 |
| 2021/0346204 A1 * | 11/2021 | Goldberg | A61F 9/029 |
| 2021/0368879 A1 * | 12/2021 | Motadel | A41D 13/1184 |
| 2022/0015472 A1 * | 1/2022 | Boza | A41D 13/1184 |
| 2022/0022574 A1 * | 1/2022 | Fosse | A41D 13/1161 |

\* cited by examiner

Origami One Piece X-Face Shield Headband Assembly - Perspective View

Origami One Piece Duo-Face Shield Tab & Notch Fasten System - Perspective View
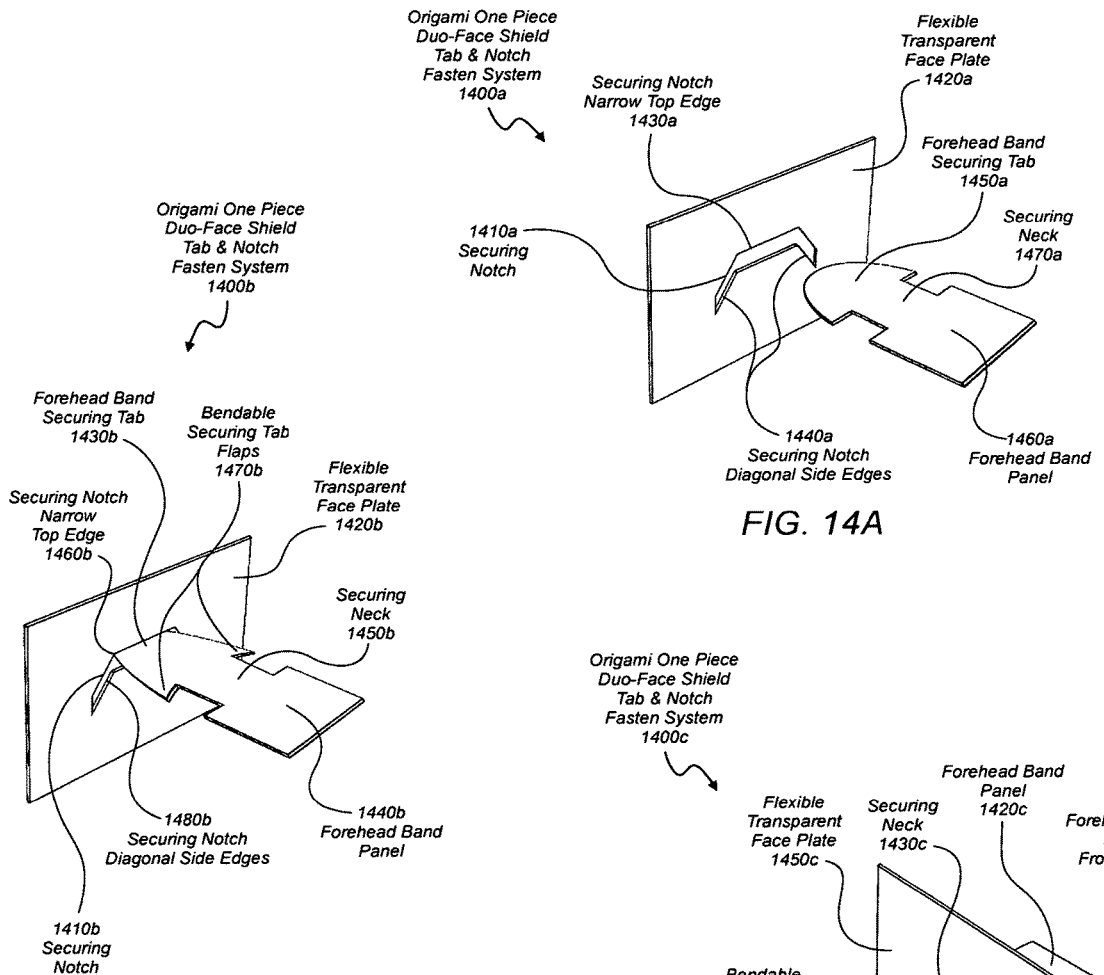
FIG. 14A
FIG. 14B
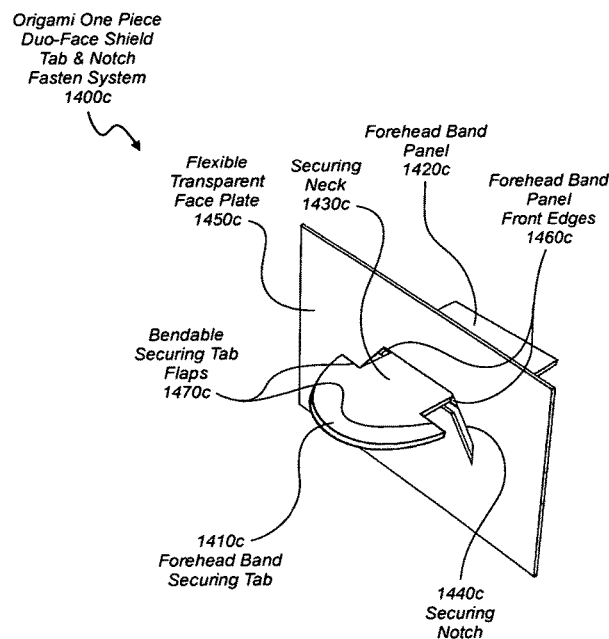
FIG. 14C

METHOD AND APPARATUS FOR A FLAT, SINGLE PIECE, FOLDABLE, COMPLETE, MEDICAL FACE SHIELD

BACKGROUND OF THE INVENTION

1. Field of the Invention

The present invention relates generally to a lightweight, disposable, ventilated, protective face shield assembly comprising a flexible transparent face plate, a forehead band component that rests on the user's forehead and functions to separate the flexible transparent face plate from the user's head creating space for a user's eyewear and a means for ventilation, and a head strap component containing a mechanism to size the assembly to a user's head circumference, all made from one, contiguous piece of transparent, flexible material.

More particularly, the invention relates to a lightweight, disposable, ventilated, medical face shield for the protection of the eyes and face of health care professionals, laboratory personnel, and other frontline and/or essential workers, from accidental exposure to infectious, and/or hazardous pathogens carrying fluids and particulate materials such as the Coronaviridae family of viruses including COVID-19 (SARS-CoV-2), SARS-CoV, MERS-CoV, etc., and also minimize the possibility of cross contamination with patients. Furthermore, the invention relates to a lightweight, disposable, ventilated, face shield for use by the general public during COVID-19 (SARS-CoV-2) pandemic to protect the user's eyes, mouth and nose from infected aerosols expelled by a carrier during normal breathing, speaking, and/or sneezing.

2. Description of the Prior Art

With the emergence of airborne transmitted, and presently incurable, diseases such as the COVID-19 (SARS-CoV-2) virus pandemic, the medical and essential worker personnel are repeatedly exposed to hazardous infectious pathogens on a daily basis. The pathogens transmitted may be any kind of microbe, and they may be spread in aerosols, dust or liquids. As with any airborne diseases that are caused via transmission through the air. The aerosols might be generated from sources of infection such as the bodily secretions of an infected person, or direct contact with material and surfaces infected by the carrier. Such infected aerosols may stay suspended in air currents long enough to travel for considerable distances; sneezes, for example, can easily project infectious droplets the full length of a bus. The protection of these professionals from nasal and oral emissions, blood, and other bodily fluids has become critical in the pandemic fight. As the eyes, nose and mouth include regions of thin and penetrable membranes, the face is an area requiring suitable protection from flying contaminants and particulates.

Certain basic requirements must be met by a facial protection device of this type. It must be lightweight and easily worn and removed. It must adequately shield the vital areas of the face while not obstructing vision. It must provide some method of ventilation as not to hamper breathing and to further avoid fogging and accumulation of moisture. In addition, it should be disposable for adequate and safe disposition of contaminants. Since such a large number of disposable face shields may be required and used in the field, ease of packaging and storage is also an important criteria.

The United States Centers for Disease Control of the U.S. Department of Health and Human Services, has issued a comprehensive series of recommendations for the prevention of COVID-19 (SARS-CoV-2) transmission in health care settings as well as the public in general. Such recommendations are applicable to the risk of exposure to all infected body fluids, although these recommendations show an increasing concern for protection of the eyes (particular conjunctiva) if aerosolization or splashing of blood or other fluids is likely to occur. Thus, according to the Centers for Disease Control, eye shields should be worn by medical personnel and health care workers to prevent blood and other body fluids from splattering into the eyes. Furthermore, eye shields should be worn by the general public in order to further protect the eye membrane of the wearer from expelled infected droplets by a carrier's sneeze. An effective eye shield must protect the eyes no matter which direction the wearer faces. Ordinary eyeglasses are not sufficient protection.

A number of factors affect the acceptance of a disposable face shield design, including comfort, ventilation, weight, ability to be securely retained in position, shipping volume, cost, and aesthetic considerations. In order to encourage the wide use of face shields that must be worn for extended periods of time, requiring them to be comfortable during the entire period of time of use among the general public, a face shield that is lightweight, cost-effective, comfortable to wear, easy to assemble and adjust, and disposable or easy-to-clean is highly desirable. For example, a face shield that allows the wearer to wear glasses under the face shield and/or a face shield that is well ventilated is desirable.

There have been many attempts to provide for an adequate visor/shield assembly. Some have flipped up, some are retracted, some are meant to be taped to a user's face, some are meant to attach to a hat or other headgear, but all previous versions were composed or relied on multiple separate parts, such as a fastener to affix a strap to the shield, to be assembled in order to function, which also increases the cost of manufacture. This makes them unnecessarily expensive, requiring the appropriate parts to be at hand and a larger volume to be shipped and stored.

Therefore, a need exists for a lightweight, low-cost face shield that provides ample ventilation, without the need of additional components for its construction and which can be manufactured at low cost and packaged compactly. The present invention satisfies those needs, as well as others, and overcomes the deficiencies of previously developed face shield designs.

The present invention allows for extended top, bottom, and side flaps as part of the unitary material that forms the face shield to cover a user's top, chin, neck and sides areas of the face. Known disposable face shields do not provide adequate protection to the user's neck and chin area. Thus, there is a need for a lightweight inexpensive, disposable, re-usable, one piece, face shield which will adequately protect the user's peripheral face areas. Current disposable face shields in the medical profession, in particular, do not provide the protection afforded by the present invention.

It is also advantageous in medical procedures to use disposable surgical equipment where possible to substantially reduce the risk of infection and the cost of sterilizing the surgical equipment. Additionally, cleaning conventional face shields of deposited chemicals, such as blood, paint, adhesives, dyes, solvents, resins, etc., is time consuming and often ineffective. Thus, disposable face shields have seen a wide application in various industries, e.g. medicine, dentistry, painting, manufacturing, and the like.

Since medical face shields are used to prevent transfer of pathogens and, during use, can become contaminated by these pathogens, disposable face shields are highly desired. To be practical, disposable face shields should be lightweight, low cost and easy to use by the wearer. Since face shield assemblies are typically a three dimensional shape when worn, a flat, contiguous, plastic material that contains all of the components of the face shield when folded and that allows all the components to be packaged and shipped in a compact, flat configuration and folded at the point of use is desirable. It is also appreciated, however, that the growing market for face shields is always in search of improved face shield designs that provide increasing utility, comfort, and style while reducing material requirements and manufacturing costs.

A disposable face shield manufacturing material may be formulated or coated with the optical ability to minimize or block certain light spectrums, such as ultraviolet, blue light, etc., to further protect the user's eyes from his/hers work environment as well as to minimize other optical phenomena as glare.

A number of examples of practical face shields exist. Examples of face shields which are being increasingly utilized in a number of industries, but that require one or more parts for its assembly and/or use, may be found in the following references; Highsmith U.S. Pat. No. 5,440,760; Burke Jr. et al U.S. Pat. No. 5,113,528; Landis U.S. Pat. No. D375,583; Lee U.S. Pat. No. 5,647,060; Landis U.S. Pat. No. 5,692,522; Machson U.S. Pat. No. 5,732,410; Desy U.S. Pat. No. 5,983,390; Landis U.S. Pat. No. 6,016,808; Reaux U.S. Pat. No. 7,540,039 B2; Reaux U.S. Pat. No. 8,261,375 B1; and Howard U.S. Pat. No. 9,949,517 B2.

Further examples of prior art that are utilized in a number of industries but, do not cover the user's full face, may be found in the following references; Saboory U.S. Pat. No. 5,584,078; Ramsey US 2006/0143766 A1; Vincent et al US 2008/0010726 A1; and Heil US 2010/0146679 A1.

Also, examples of prior art that require one or more parts for its assembly and use, and that do not cover the user's full face, maybe be found in the following references; Kuntz et al U.S. Pat. No. 4,825,878; Borek Jr. U.S. Pat. No. 4,944,294; Hubbard et al U.S. Pat. No. 5,150,703; and Baker et al U.S. Pat. No. 5,446,925, all of which are incorporated herein by reference.

The above face shields provide numerous benefits. It will be appreciated, however, that the growing market for face shields is always in search of improved face shield designs that provide increasing utility, comfort, and style while reducing material requirements, manufacturing costs, package volume requirements and therefore, reduce shipping costs and storage space requirements. It is to the provision of such, therefore, that the present invention is primarily directed.

SUMMARY OF THE INVENTION

The present invention mitigates the limitations of the prior art by providing a lightweight, self-contained, one piece, disposable, ventilated, face shield for the protection of regions of thin and penetrable membranes, such as the eyes, nose and mouth of medical personnel, essential workers and the general public from exposure to infectious, and/or hazardous pathogens carrying fluids and particulate materials such as the Coronaviridae family of viruses including COVID-19 (SARS-CoV-2), SARS-CoV, MERS-CoV, etc., and also, to minimize the possibility of cross contamination from infected aerosols expelled by a patient/carrier during normal breathing, speaking, and/or sneezing, that obviates the need for any supplementary parts or materials for its final assembly, and that due to its flat construction, can be more cost efficiently manufactured, packaged, shipped, and then assembled at the point of use.

The face shield comprises a fluid-impervious, flexible, transparent, face plate component for the frontal protection of the wearers eyes, mouth and nose from exposure to liquid and airborne infectious contaminants; also a forehead component that creates a gap between the user's forehead and the top of the transparent face plate component for added comfort, eyeglass use, and expiration ventilation; a head strap component to securely size and comfortably attach the face shield to the user's head via a slot and notch system; and a series of foldable, top, side, and bottom flaps to further protect the user's face from angled contaminants.

It is an object and advantage of the present invention to provide a complete face shield that provides all the necessary components in one, flat, contiguous, light weight, disposable piece of transparent material that can be folded into a 3-dimensional form by the end user without the need for any external materials or components for its final construction.

It is further object and advantage of the present invention to provide a face shield with an integrated forehead component which is in contact with the forehead of the wearer and serves to create a space between the face shield's face plate and the user's face for improved ventilation, reduce fogging and to accommodate the use of eyeglasses.

One embodiment of the invention is characterized in that the forehead component is assembled by folding, crossing and connecting the right and left forehead bands resulting in a combined total diameter shorter than the total diameter of the top of the transparent face plate, resulting in an arcuate shape, that provides the spacing between the user's forehead and the transparent face plate component for ventilation and eyeglass use.

Another embodiment of the invention is characterized in that the forehead band component is assembled by folding the panels of the forehead band component and attaching and securing them in place to the transparent face plate by a tab and notch system, creating an arcuate forehead rest plate that provides the spacing between the user's forehead and the transparent face plate component for ventilation and eyeglass use.

It is further object and advantage of the present invention to provide a face shield with an integrated head strap component to comfortably size the head band and attach it to the user's head.

Another further object and advantage of the present invention is to provide a face shield which can provide further protection to the user's top, chin, neck and sides of the head by the use of integrated, foldable flaps.

Another further object and advantage of the present invention is to provide a face shield which can be worn with eyeglasses, a surgical mask, some head gear, etc.

Still, another further object and advantage of the present invention is to provide a face shield which will diminish mist caused by nasal and mouth expiration.

Another further object and advantage of the present invention is to provide a face shield which can provide further optical protections such as glare, ultra-violet rays, blue light, radiation, etc., to the user's eyes.

Another further object and advantage of the present invention is that the shield may be fabricated of a plastic material that has been coated with an anti-fog agent to prevent the wearer's breath from fogging up the shield when worn.

A still further object and advantage of the present invention is to provide a face shield which is adapted to display an image, text, advertisement, and/or other messages within its form.

Another object of the present invention is to provide a face shield which may be disposable.

Another object and advantage of the present invention is to provide a face shield which can be easily cleaned, sterilized and re-used, if needed.

Another object and advantage of the present invention is to provide a face shield which can be easily recycled.

A still further object and advantage of the present invention is to provide a face shield which is inexpensive to manufacture and acquire compared to prior art.

Another object and advantage of the present invention is to provide a complete face shield that can be shipped in a flat profile, thus greatly saving manufacturing, packaging volume, and shipping costs compared to prior art.

Further aspects and advantages of the present invention will be obvious upon an understanding of the illustrative embodiments about to be described or will be indicated in the appended claims. The drawings constitute a part of this specification and include exemplary embodiments to the invention, which may be embodied in various forms. Various advantages not referred to herein will occur to one skilled in the art upon employment of the invention in practice. It is to be understood that in some instances various aspects of the invention may be shown exaggerated or enlarged to facilitate an understanding of the invention, wherein the detailed description is for the purpose of fully disclosing preferred embodiments of the invention without placing limitations thereon.

BRIEF DESCRIPTION OF THE DRAWINGS

FIG. 14A illustrates a perspective close up view of the Origami One Piece Duo-Face Shield Tab & Notch system main parts for an embodiment of the origami one piece face shield.

FIG. 14B illustrates a perspective close up view of the Origami One Piece Duo-Face Shield Tab & Notch system main parts being attached for an embodiment of the origami one piece face shield.

FIG. 14C illustrates a perspective close up view of the Origami One Piece Duo-Face Shield Tab & Notch system main parts securely attached for an embodiment of the origami one piece face shield.

DETAIL DESCRIPTION

Origami One Piece X-Face Shield

Figure 1:
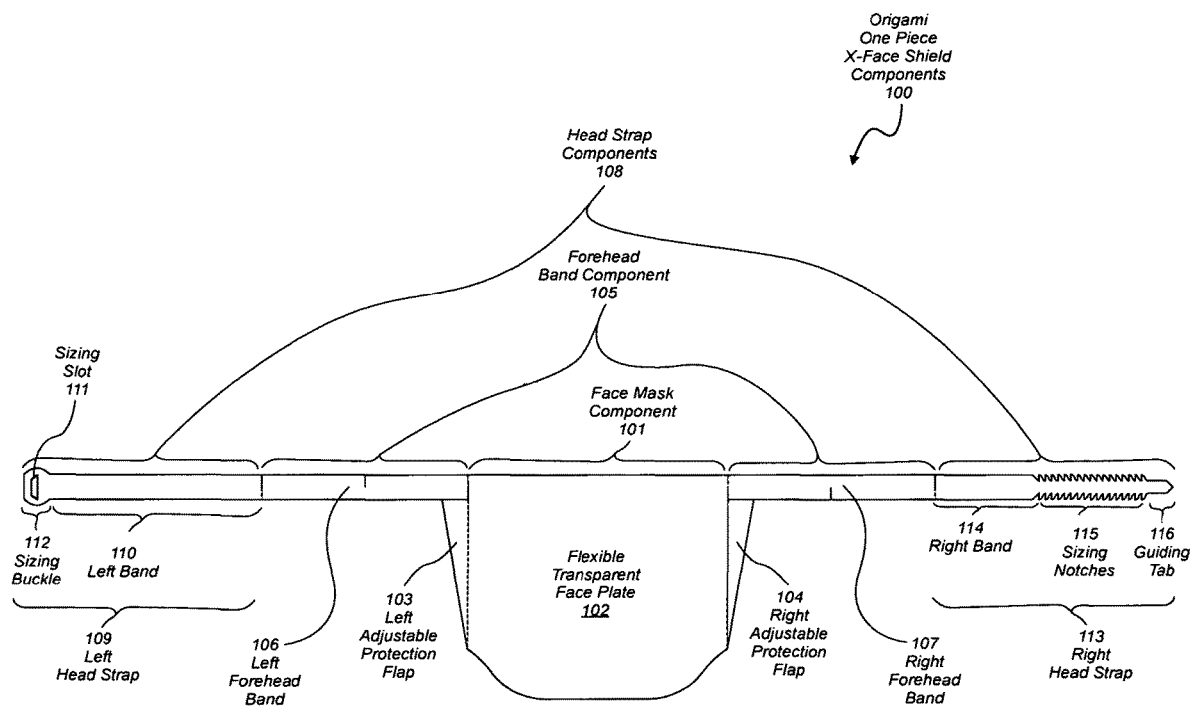
FIG. 1 illustrates an orthographic view of the Origami One Piece X-Face Shield main components for an embodiment of the origami one piece face shield.

FIG. 1 illustrates an orthographic view of the Origami One Piece X-Face Shield components 100. FIG. 1 shows an orthographic view of the basic components of the Origami One Piece X-Face Shield 100, including, the face mask component 101, that incorporates, but is not limited to, the flexible transparent face plate 102, the left adjustable protection flap 103, and the right adjustable protection flap 104. FIG. 1 shows an orthographic view of the forehead band component 105, that includes, but is not limited to, the left forehead band 106, and the right forehead band 107. FIG. 1 shows an orthographic view of the head strap component 108, that includes, but is not limited to, the left head strap 109, that incorporates, the left band 110, and the sizing buckle 112, with a sizing slot 111, and the right head strap 113, that incorporates, the right band 114, the sizing notches 115, and the guiding tab 116.

Figure 2:
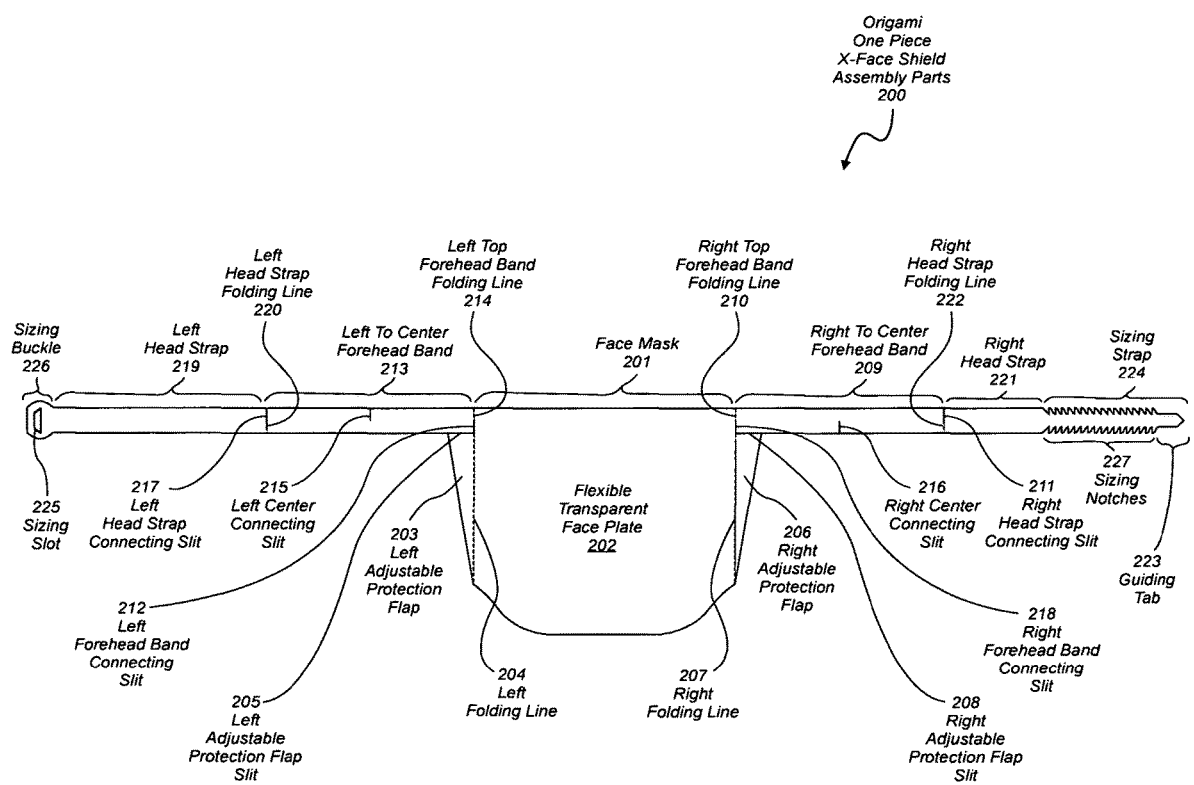
FIG. 2 illustrates an orthographic view of the Origami One Piece X-Face Shield assembly parts for an embodiment of the origami one piece face shield.

FIG. 2 illustrates an orthographic view of the Origami One Piece X-Face Shield assembly parts 200. FIG. 2 shows an orthographic view of the basic assembly parts of the Origami One Piece X-Face Shield 200, including, the face mask 201, that includes, but is not limited to, the flexible transparent face plate 202, the left adjustable protection flap 203, that pivots along the left folding line 204, and detaches along the left adjustable protection flap slit 205, from the main body, and the right adjustable protection flap 206, that pivots along the right folding line 207, and detaches along the right adjustable protection flap slit 208, from the main body. FIG. 2 shows the right to center forehead band 209, that pivots along the right top forehead band folding line 210, allowing the right head strap connecting slit 211, to connect to the left forehead band connecting slit 212. FIG. 2 shows the left to center forehead band 213, that pivots along the left top forehead band folding line 214, allowing the left center connecting slit 215, to connect to the right center connecting slit 216, and the left head strap connecting slit 217, to connect to the right forehead band connecting slit 218. FIG. 2 shows the left head strap 219, that pivots along the left head strap folding line 220, and the right head strap 221, that folds along the right head strap folding line 222, allowing the guiding tab 223, part of the sizing strap 224, to be inserted into the sizing slot 225, of the sizing buckle 226, along with the sizing notches 227, to adjust the head strap components (see FIG. 1, head strap components 108), to the user's head size.

Figure 3:
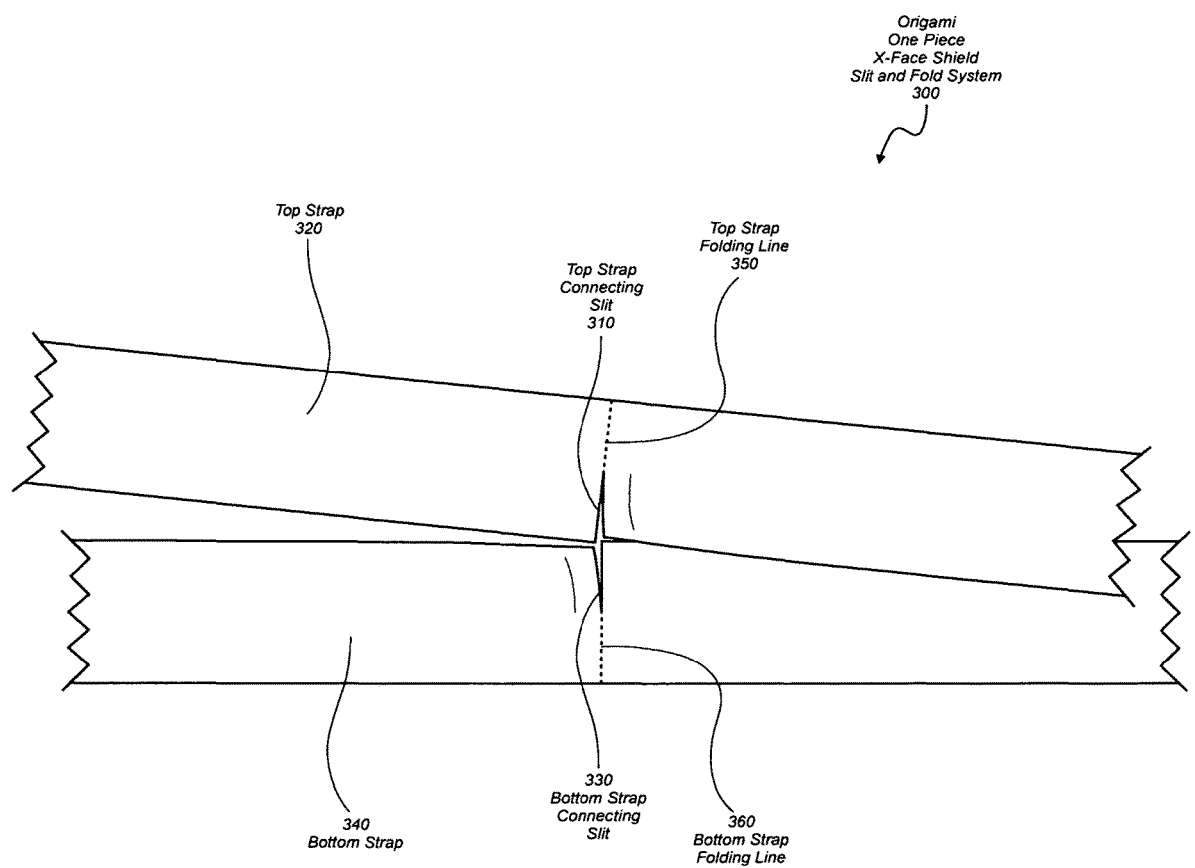
FIG. 3 illustrates a perspective close up view of the Origami One Piece X-Face Shield Slit and Fold System for an embodiment of the origami one piece face shield.

FIG. 3 illustrates a perspective close-up view of the Origami One Piece X-Face Shield slit and fold system 300. FIG. 3 shows the Origami One Piece X-Face Shield slit and fold system 300, including the top strap connecting slit 310, of the top strap 320, that opens and intersects with the open bottom strap connecting slit 330, of the bottom strap 340, as a means of attachment in the face mask assembly. FIG. 3 shows that the top strap 320, may be folded along the top strap folding line 350, parallel to the top strap connecting slit 310, and the bottom strap connecting slit 330, at an angle from the bottom strap 340, as a means of assembly. FIG. 3 shows that the bottom strap 340, may be folded along the bottom strap folding line 360, parallel to the bottom strap connecting slit 330, and the top strap connecting slit 310, at an angle from the top strap 320, as a means of assembly.

Figure 4:
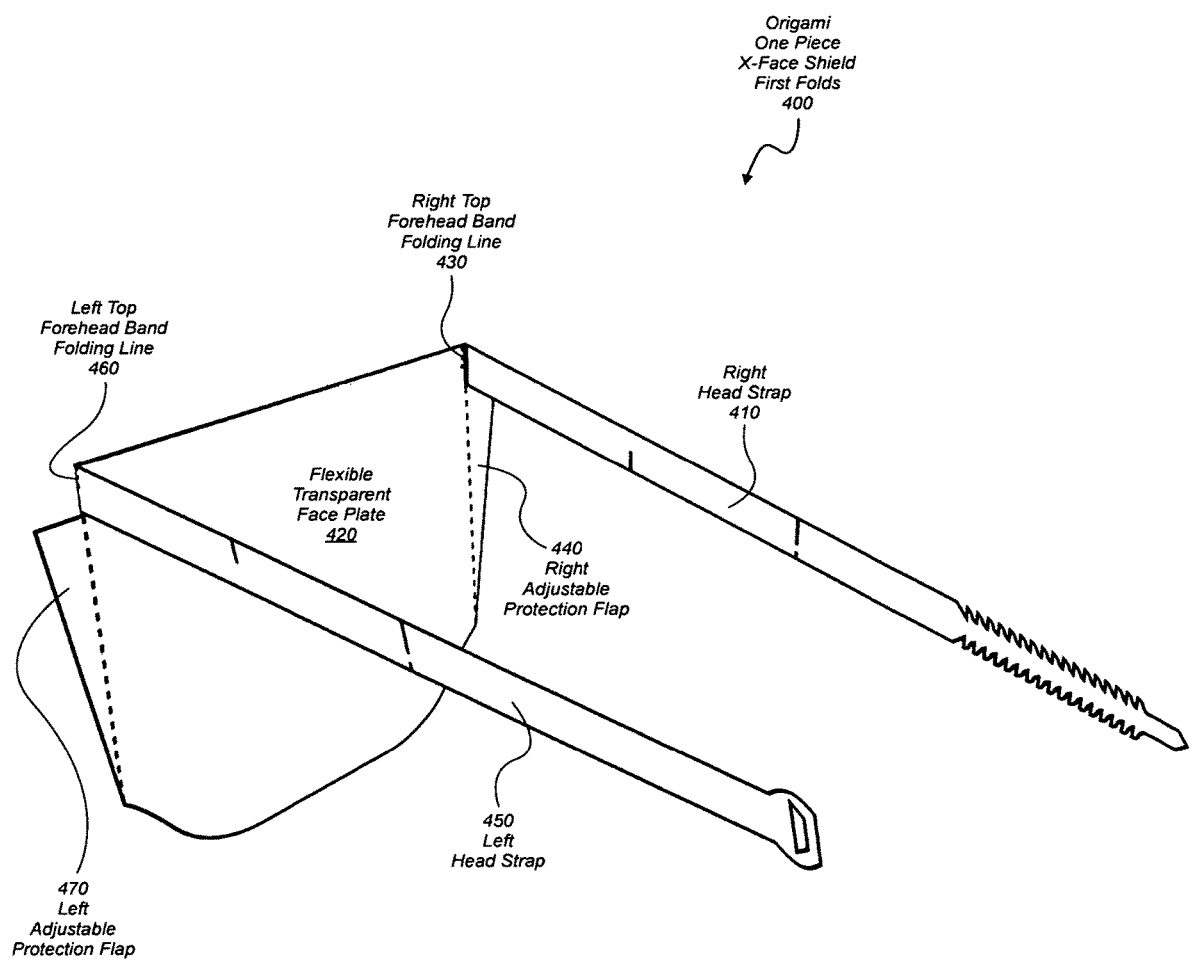
FIG. 4 illustrates a perspective view of the first fold of the Origami One Piece X-Face Shield to create the forehead band component of the face shield for an embodiment of the origami one piece face shield.

FIG. 4 illustrates a perspective view of the Origami One Piece X-Face Shield first folds 400. FIG. 4 shows the Origami One Piece X-Face Shield first folds 400, including folding the right head strap 410, connected to the flexible transparent face plate 420, pivoting along the right top forehead band folding line 430, to a perpendicular position relative to the flexible transparent face plate 420, vertical plane, detaching from the right adjustable protection flap 440. FIG. 4 shows an orthographic view of the left head strap 450, connected to the flexible transparent face plate 420, folds and pivots along the left top forehead band folding line 460, to a perpendicular position relative to the flexible transparent face plate 420, vertical plane detaching from the left adjustable protection flap 470.

Figure 5:
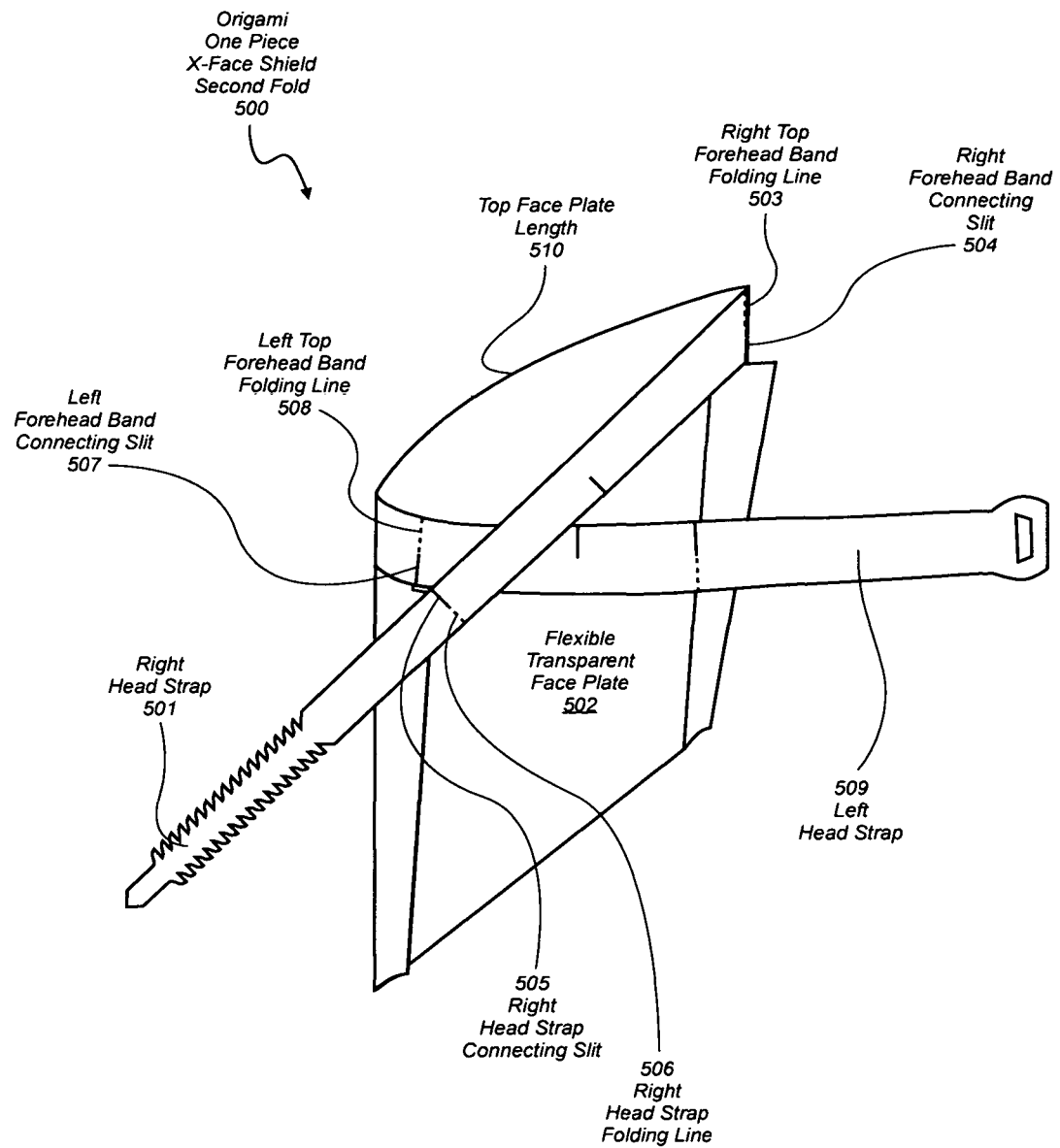
FIG. 5 illustrates a perspective view of the second fold of the Origami One Piece X-Face Shield to create the forehead band component of the face shield for an embodiment of the origami one piece face shield.

FIG. 5 illustrates a perspective view of the Origami One Piece X-Face Shield second fold 500. FIG. 5 shows a perspective view of the Origami One Piece X-Face Shield second fold 500, including folding the right head strap 501, connected to the flexible transparent face plate 502, pivoting along the right top forehead band folding line 503, parallel to the right forehead band connecting slit 504, and inserting the right head strap connecting slit 505, that is parallel to the right head strap folding line 506, into the left forehead band connecting slit 507, that is parallel to the right head band folding line 508, of the left head strap 509. FIG. 5 illustrates a perspective view that the resulting incidental length of the forehead band components (see FIG. 1, forehead band components 105), is shorter than the length of the top face plate length 510, creating a curved gap between the user's forehead and the flexible transparent face plate 502, when assembled, for ventilation.

Figure 6:
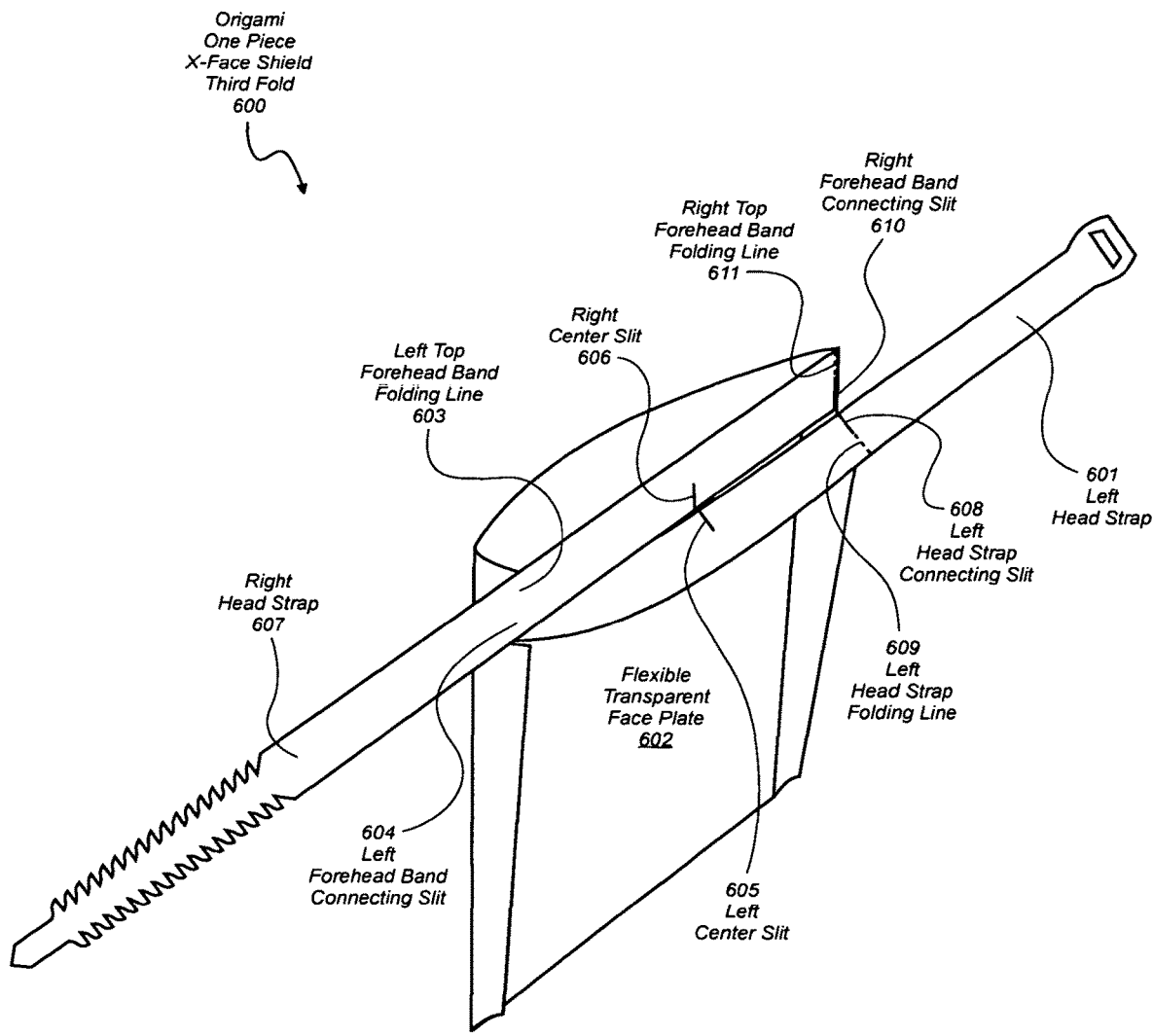
FIG. 6 illustrates a perspective view of the third fold of the Origami One Piece X-Face Shield to create the forehead band component of the face shield for an embodiment of the origami one piece face shield.

FIG. 6 illustrates a perspective view of the Origami One Piece X-Face Shield third fold 600. FIG. 6 shows a perspective view the Origami One Piece X-Face Shield third fold 600, including folding the left head strap 601, connected to the flexible transparent face plate 602, pivoting along the left top forehead band folding line 603, parallel to the left forehead band connecting slit 604, and inserting the left center slit 605, into the right center slit 606, of the right head strap 607, and the left head strap connecting slit 608, parallel to the left head strap folding line 609, of the left head strap 601, into the right forehead band connecting slit 610, parallel to the right top forehead band folding line 611, of the right head strap 607, reinforcing the forehead band component (see FIG. 1, forehead band components 105), of the face shield.

Figure 7:
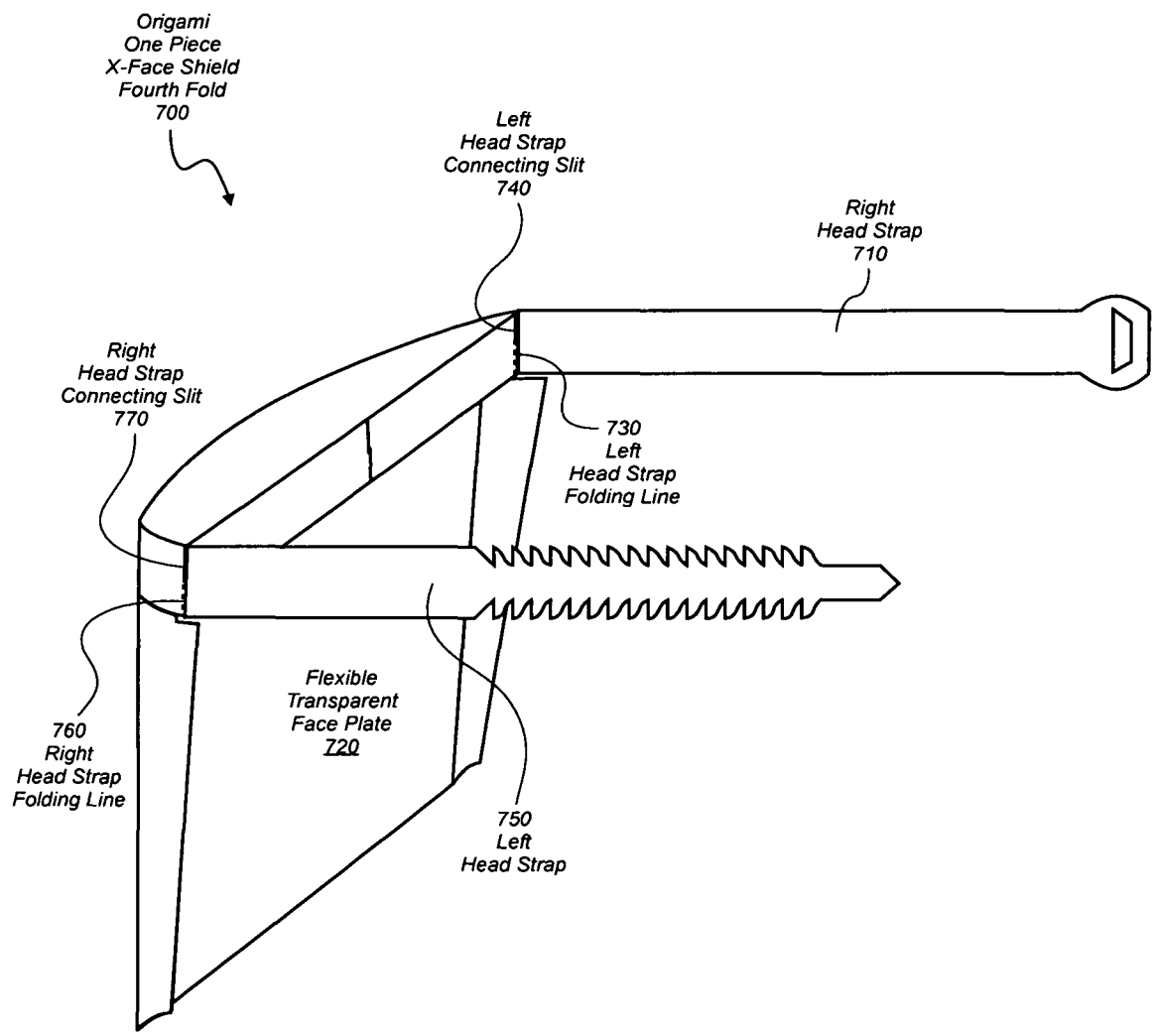
FIG. 7 illustrates a perspective view of the fourth fold of the Origami One Piece X-Face Shield to create the head strap component of the face shield for an embodiment of the origami one piece face shield.

FIG. 7 illustrates a perspective view of the Origami One Piece X-Face Shield fourth fold 700. FIG. 7 shows a perspective view of the Origami One Piece X-Face Shield fourth fold 700, including folding the right head strap 710, connected to the flexible transparent face plate 720, pivoting along the left head strap folding line 730, parallel to the left head strap connecting slit 740, to a perpendicular position relative to the flexible transparent face plate 720, vertical plane. FIG. 7 shows a perspective view of the left head strap 750, connected to the flexible transparent face plate 720, folding and pivoting along the right head strap folding line 760, parallel to the right head strap connecting slit 770, to a perpendicular position relative to the flexible transparent face plate 720, vertical plane.

Figure 8:
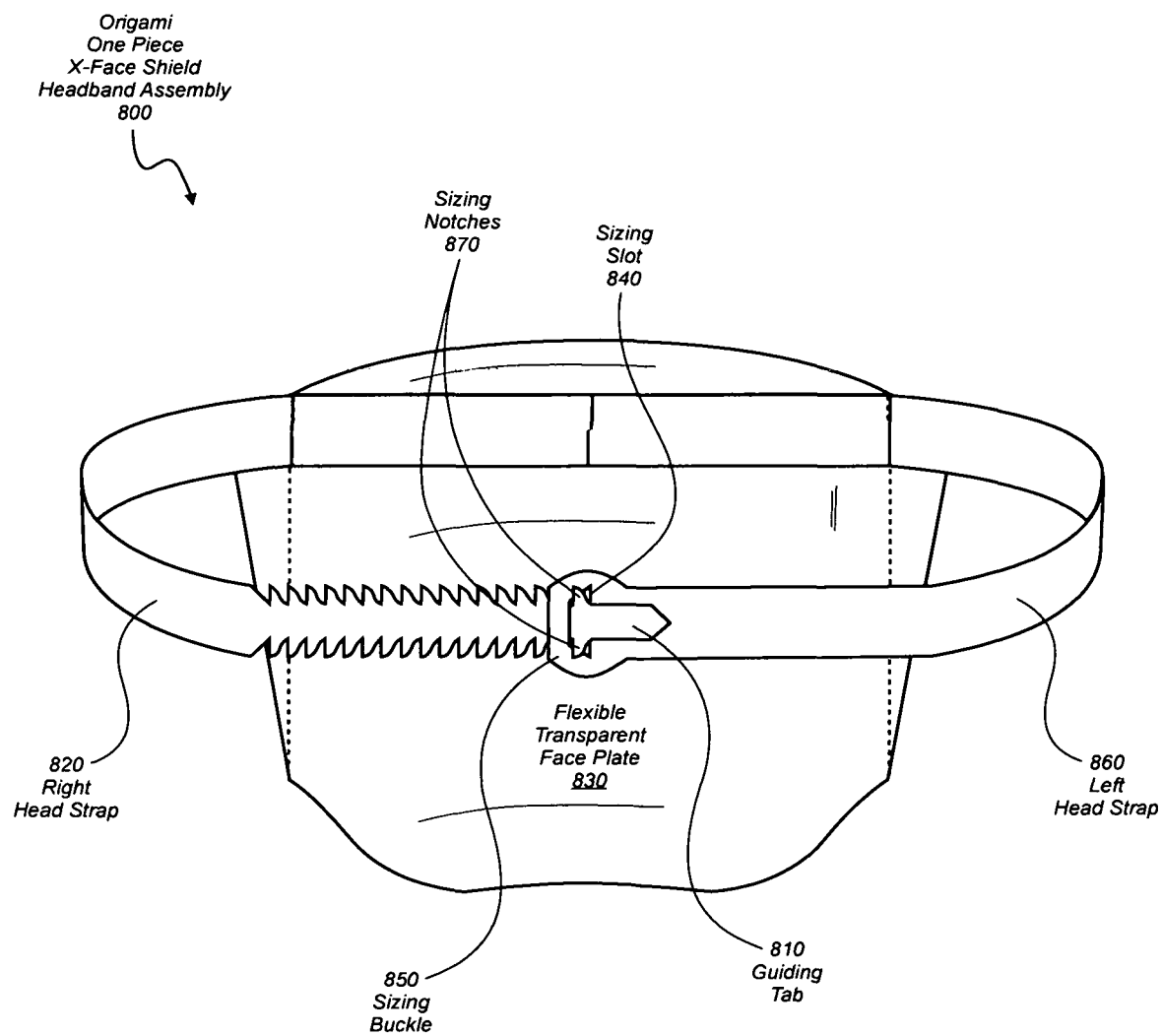
FIG. 8 illustrates a perspective view for an embodiment of the Origami One Piece X-Face Shield headband assembly parts for an embodiment of the origami one piece face shield.

FIG. 8 illustrates a perspective view of the Origami One Piece X-Face Shield headband assembly 800. FIG. 8 shows a perspective view of the Origami One Piece X-Face Shield headband assembly 800, including the guiding tab 810, of the right head strap 820, connected to the flexible transparent face plate 830, inserted into the sizing slot 840, of the sizing buckle 850, of the left head strap 860, until it reaches and locks the sizing notches 870, forming the basic head band component (see FIG. 1, head strap components 108), of the face shield.

Figure 9:
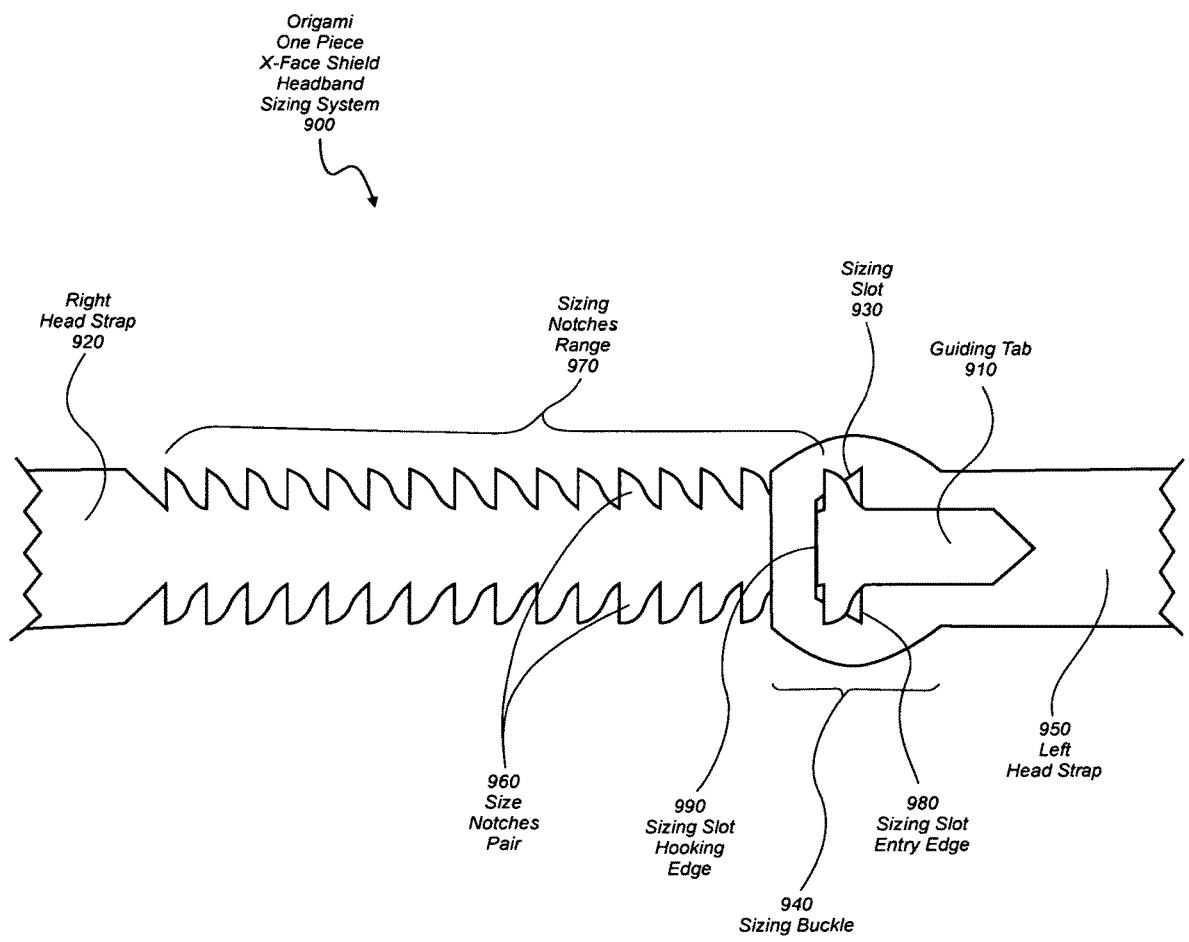
FIG. 9 illustrates a perspective close up view of the Origami One Piece X-Face Shield headband sizing system for an embodiment of the origami one piece face shield.

FIG. 9 illustrates a perspective close-up view of the Origami One Piece X-Face Shield headband sizing system 900. FIG. 9 shows a perspective view of the Origami One Piece X-Face Shield headband sizing system 900, including the guiding tab 910, of the right head strap 920, inserted into the sizing slot 930, of the sizing buckle 940, of the left head strap 950, and pass the size notches pairs 960, of the sizing notches range 970, of the right head strap 920, by the wider, sizing slot entry edge 980, until it reaches the user's head diameter, and the size notches pair 960, slides back and locks into the narrow, sizing slot hooking edge 990.

Figure 10:
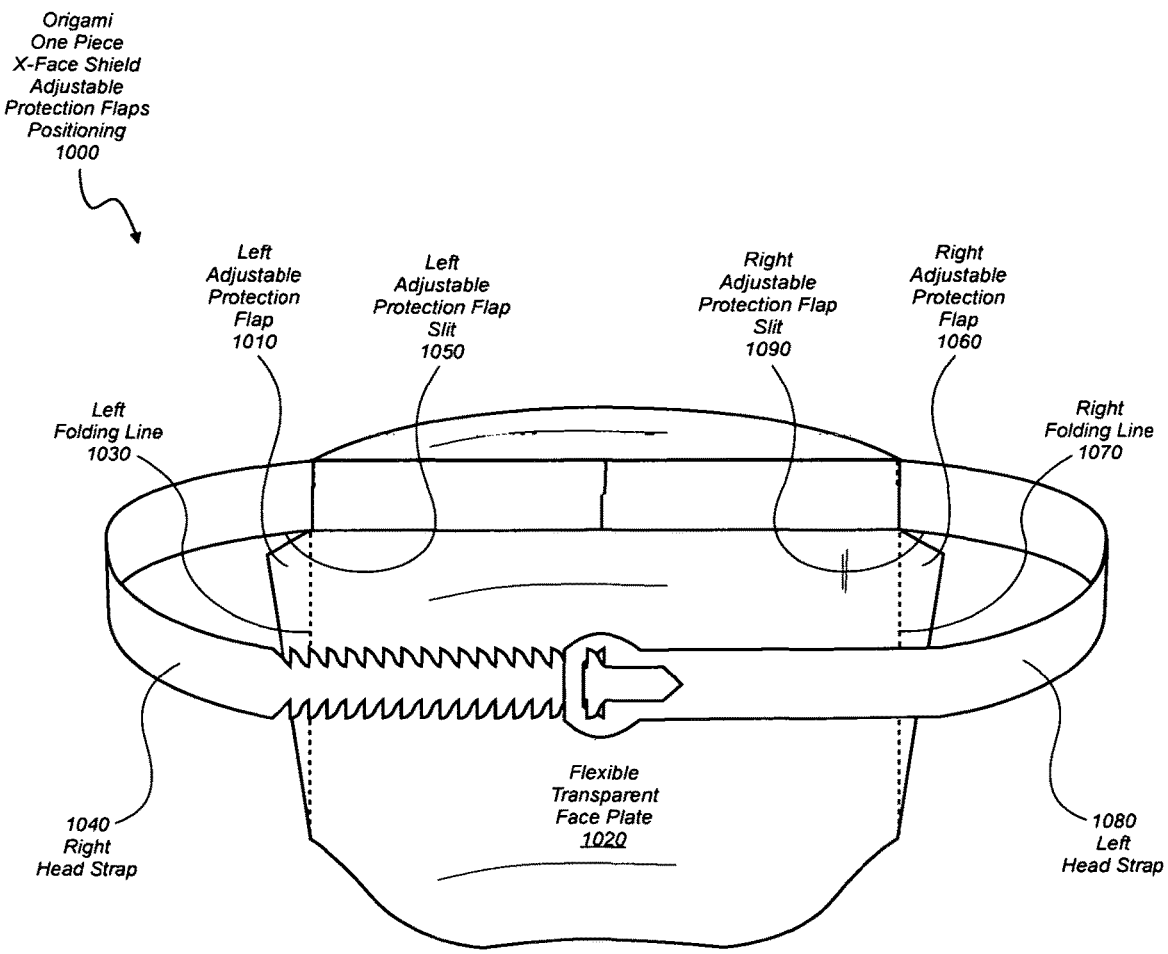
FIG. 10 illustrates a perspective view of the Origami One Piece X-Face Shield adjustable protection flaps positioning for an embodiment of the origami one piece face shield.

FIG. 10 illustrates a perspective view of the Origami One Piece X-Face Shield adjustable protection flaps positioning 1000. FIG. 10 shows a perspective view of the Origami One Piece X-Face Shield adjustable protection flaps positioning 1000, including folding the left adjustable protection flap 1010, connected to the flexible transparent face plate 1020, along the left folding line 1030, as it detaches from the right head strap 1040, to a perpendicular position relative to the flexible transparent face plate 1020, vertical plane, along the left adjustable protection flap slit 1050. FIG. 10 shows a perspective view of the right adjustable protection flap 1060, connected to the flexible transparent face plate 1020, along the right folding line 1070, as it detaches from the left head strap 1080, to a perpendicular position relative to the flexible transparent face plate 1020, vertical plane, along the right adjustable protection flap slit 1080.

Origami One Piece Duo-Face Shield

Figure 11:
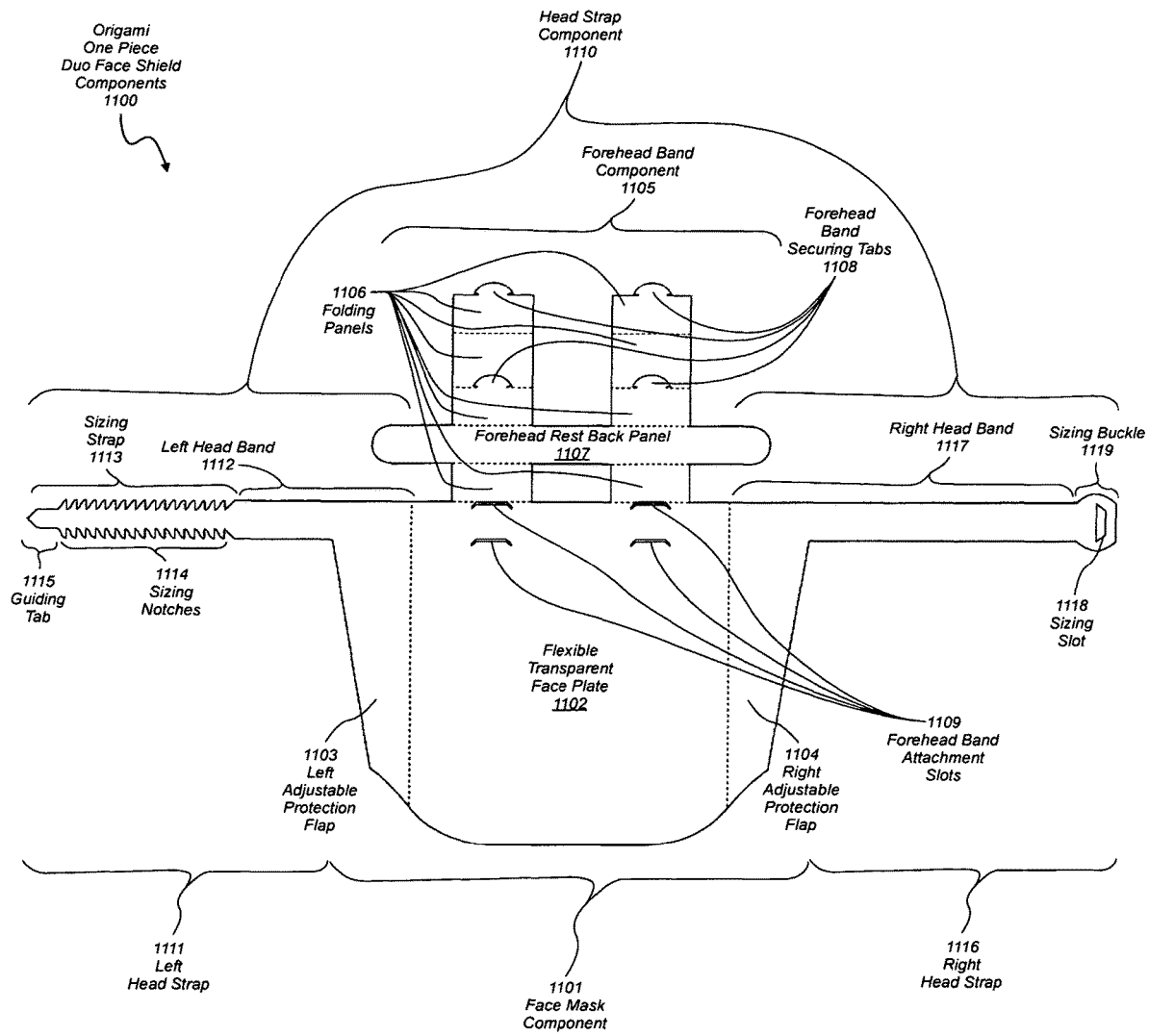
FIG. 11 illustrates an orthographic view of the Origami One Duo-Face Shield main components for an embodiment of the origami one piece face shield.

FIG. 11 illustrates an orthographic view of the Origami One Piece Duo-Face Shield components 1100. FIG. 11 shows an orthographic view of the basic components of the Origami One Piece Duo-Face Shield 1100, including, the face mask component 1101, that incorporates, but is not limited to, the flexible transparent face plate 1102, the left adjustable protection flap 1103, and the right adjustable protection flap 1104. FIG. 11 shows an orthographic view of the forehead band component 1105, that includes, but is not limited to, the folding panels 1106, the forehead rest back panel 1107, the forehead band securing tabs 1108, and the forehead band attachment slots 1109. FIG. 11 shows an orthographic view of the head strap component 1110, that includes, but is not limited to, the left head strap 1111, that incorporates, the left head band 1112, and the sizing strap 1113, that incorporates, the sizing notches 1114, and the guiding tab 1115. FIG. 11 shows the head strap component 1110, that includes, but is not limited to, the right head strap 1116, that incorporates, the right head band 1117, and the sizing slot 1118, within the sizing buckle 1119.

Figure 12:
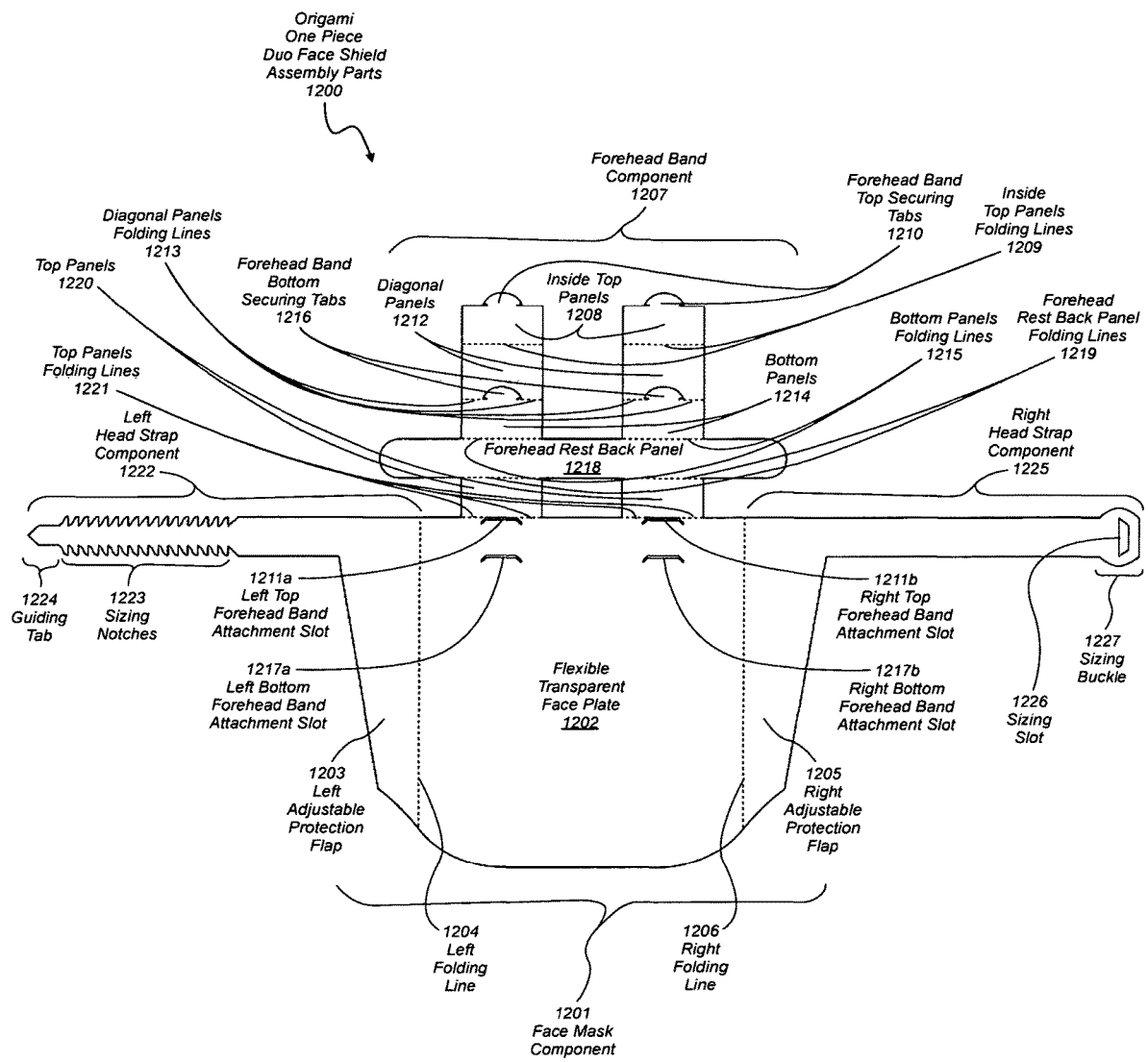
FIG. 12 illustrates an orthographic view of the Origami One Piece Duo-Face Shield assembly parts for an embodiment of the origami one piece face shield.

FIG. 12 illustrates an orthographic view of the Origami One Piece Duo-Face Shield assembly parts 1200. FIG. 12 shows an orthographic view of the basic assembly parts of the Origami One Piece Duo-Face Shield 1200, including, the face mask component 1201, that incorporates, but is not limited to, the flexible transparent face plate 1202, the left adjustable protection flap 1203, that pivots along the left folding line 1204, and the right adjustable protection flap 1205, that pivots along the right folding line 1206. FIG. 12 shows an orthographic view of the forehead band component 1207, that incorporates, but is not limited to, the inside top panels 1208, with their inside top panels folding lines 1209, and topped by their forehead band top securing tabs 1210, that inserts into the left top forehead band attachment slot 1211a, and the right top forehead band attachment slot 1211b, respectively. FIG. 12 shows an orthographic view of the forehead band component 1207, that incorporates, but is not limited to, the diagonal panels 1212, with their diagonal panels folding lines 1213. FIG. 12 shows an orthographic view of the forehead band component 1207, that incorporates, but is not limited to, the bottom panels 1214, with their bottom panels folding lines 1215, and topped by their forehead band bottom securing tabs 1216, that inserts into the left bottom forehead band attachment slot 1217a, and the right bottom forehead band attachment slot 1217b, respectively. FIG. 12 shows an orthographic view of the forehead band component 1207, that incorporates, but is not limited to, the forehead rest back panel 1218, with its forehead rest back panel folding lines 1219. FIG. 12 shows an orthographic view of the forehead band component 1207, that incorporates, but is not limited to, the top panels 1220, with its top panels folding lines 1221. FIG. 12 shows the left head strap component 1222, that incorporates, but is not limited to, the sizing notches 1223, and the guiding tab 1224. FIG. 12 shows an orthographic view of the right head strap component 1225, that incorporates, but is not limited to, the sizing slot 1226, within the sizing buckle 1227.

Figure 13:
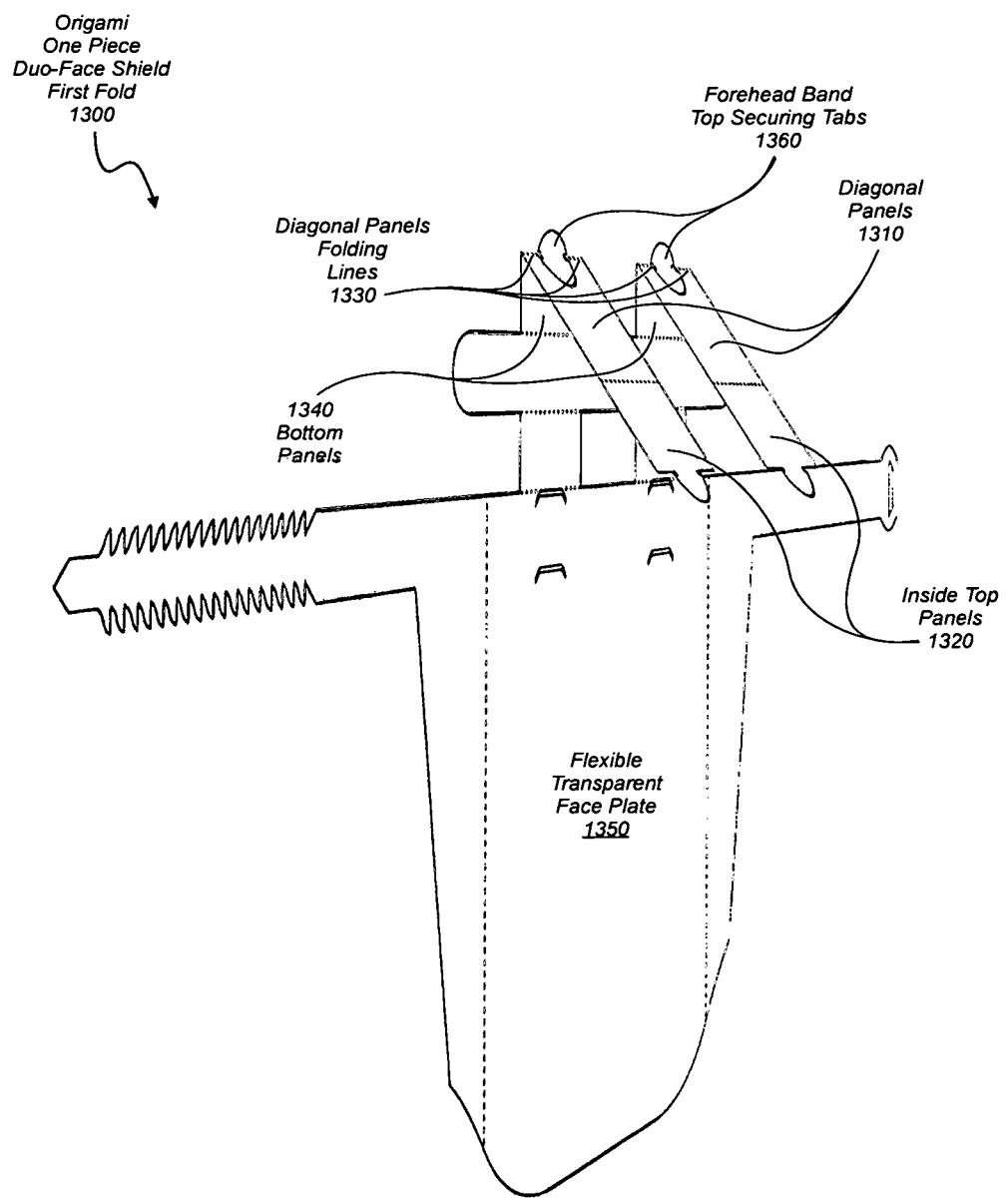
FIG. 13 illustrates a perspective view of the first fold of the Origami One Piece Duo-Face Shield to create the forehead band component of the face shield for an embodiment of the origami one piece face shield.

FIG. 13 illustrates a perspective view of the Origami One Piece Duo-Face Shield first fold 1300. FIG. 13 shows a perspective view of the Origami One Piece Duo-Face Shield first folds 1300, including folding the diagonal panels 1310, that are topped by the inside top panels 1320, by the diagonal panels folding lines 1330, at a tangential angle angle from the bottom panels 1340, that are connected to the flexible transparent face plate 1350, exposing the forehead band top securing tab 1360.

FIG. 14A illustrates a perspective view of the Origami One Piece Duo-Face Shield tab & notch fasten system 1400a. FIG. 14A shows a perspective view of the Origami One Piece Duo-Face Shield tab & notch fasten system 1400a, including the securing notch 1410a, within the flexible transparent face plate 1420a, that incorporates a securing notch narrow top edge 1430a, and the securing notch diagonal side edges 1440a. FIG. 14A shows a perspective view of the Origami One Piece Duo-Face Shield tab & notch fasten system 1400a, including the forehead band securing tab 1450a, connected to the forehead band panel 1460a, by the securing neck 1470a.

FIG. 14B illustrates a perspective view of the Origami One Piece Duo-Face Shield tab & notch fasten system 1400b. FIG. 14B shows a perspective view of the Origami One Piece Duo-Face Shield tab & notch fasten system 1400b, including the securing notch 1410b, within the flexible transparent face plate 1420b. FIG. 14B shows a perspective view of the Origami One Piece Duo-Face Shield tab & notch fasten system 1400b, including the forehead band securing tab 1430b, connected to the forehead band panel 1440b, by the securing neck 1450b, as it is inserted into the securing notch 1410b, through the securing notch narrow top edge 1460b, and the bendable securing tab flaps 1470b, bend down and through the securing notch diagonal side edges 1480b.

FIG. 14C illustrates a perspective view of the Origami One Piece Duo-Face Shield tab & notch fasten system 1400c. FIG. 14C shows a perspective view of the Origami One Piece Duo-Face Shield tab & notch fasten system 1400c, including the forehead band securing tab 1410c, connected to the forehead band panel 1420c, by the securing neck 1430c, as it is inserted past the securing notch 1440c, within the flexible transparent face plate 1450c, until it reaches the forehead band panel front edges 1460c, and the bendable securing tab flaps 1470c, spring open, locking it into position.

Figure 15:
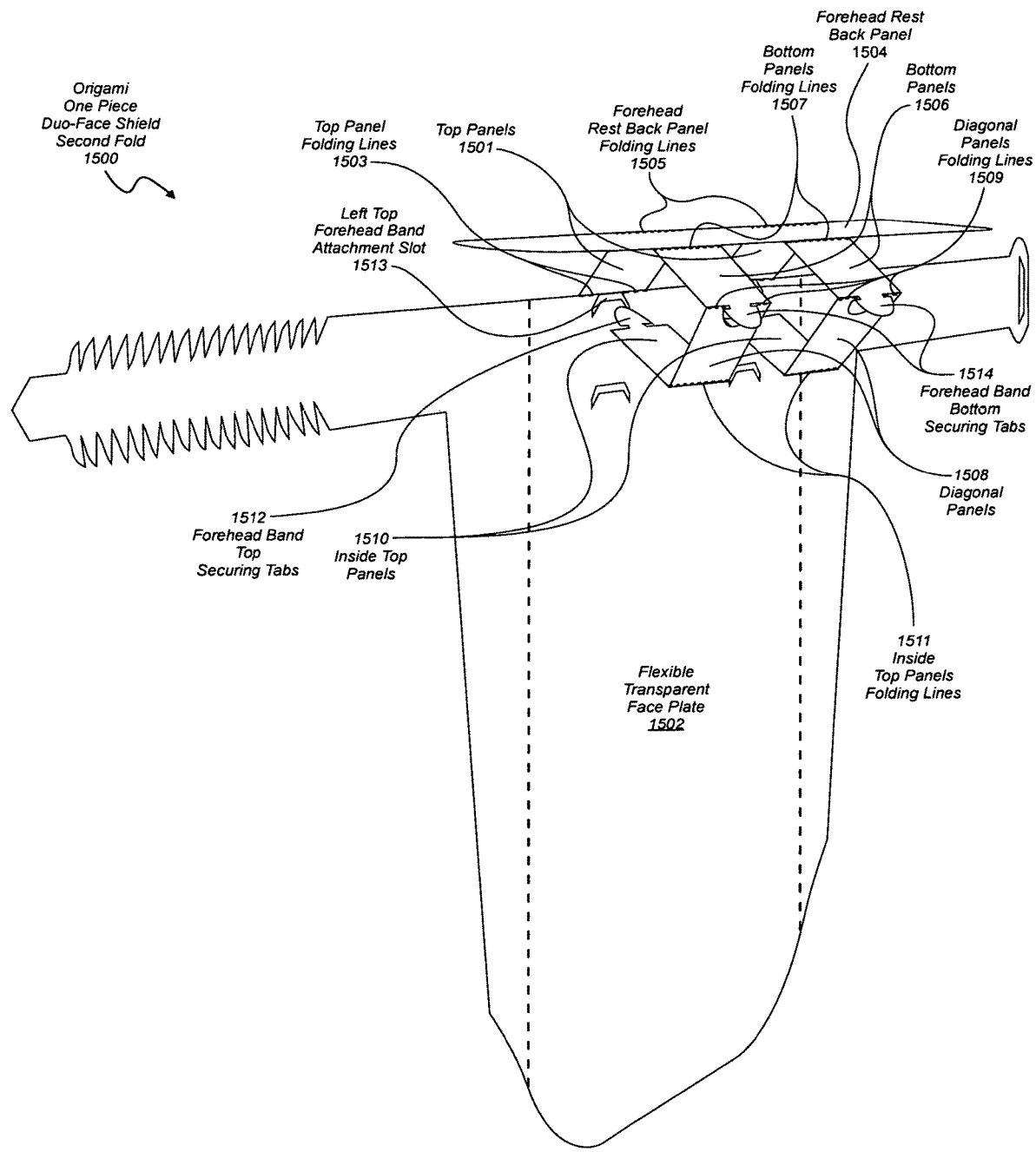
FIG. 15 illustrates a perspective view of the second fold of the Origami One Piece Duo-Face Shield to create the forehead band component of the face shield for an embodiment of the origami one piece face shield.

FIG. 15 illustrates a perspective view of the Origami One Piece Duo-Face Shield second fold 1500. FIG. 15 shows a perspective view of the Origami One Piece Duo-Face Shield second fold 1500, including the top panels 1501, connected to the flexible transparent face plate 1502, and folded along the top panel folding lines 1503. FIG. 15 shows a perspective view of the Origami One Piece Duo-Face Shield second fold 1500, including the forehead rest back panel 1504, folded along the forehead rest back panel folding lines 1505. FIG. 15 shows a perspective view of the Origami One Piece Duo-Face Shield second fold 1500, including the bottom panels 1506, folded along the bottom panels folding line 1507. FIG. 15 shows a perspective view of the Origami One Piece Duo-Face Shield second fold 1500, including the diagonal panels 1508, folded along the diagonal panels folding line 1509, and pushed toward the forehead rest back panel 1504, as the inside top panels 1510, angles parallel to the top panels 1501, horizontal plane, as it pivots along the inside top panels folding lines 1511, inserting the forehead band top securing tabs 1512, into the left top forehead band attachment slot 1513, and into the right top forehead band attachment slot (not shown), exposing the forehead band bottom securing tabs 1514.

Figure 16:
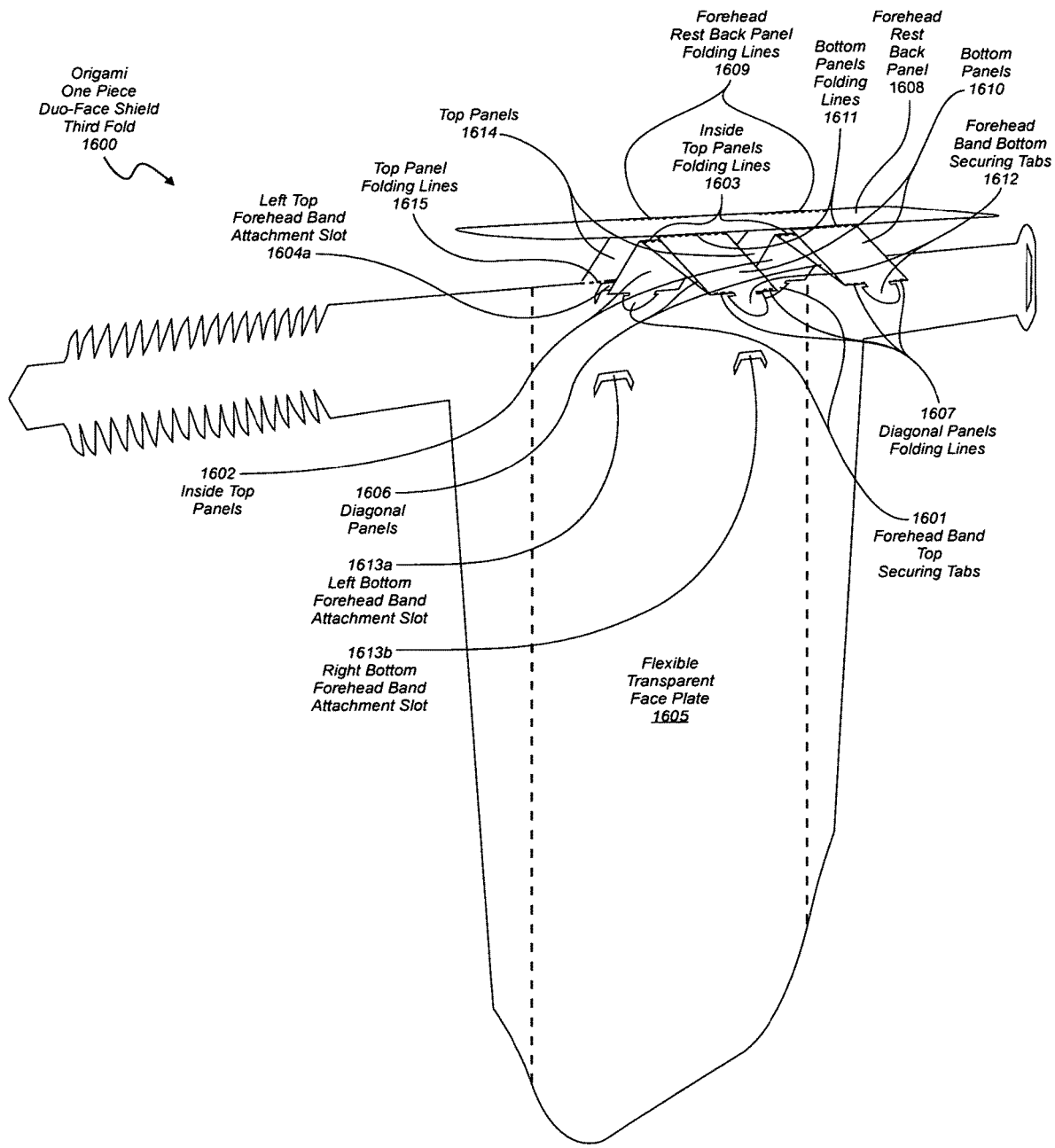
FIG. 16 illustrates a perspective view of the third fold of the Origami One Piece Duo-Face Shield to create the forehead band component of the face shield for an embodiment of the origami one piece face shield.

FIG. 16 illustrates a perspective view of the Origami One Piece Duo-Face Shield third fold 1600. FIG. 16 shows a perspective view of the Origami One Piece Duo-Face Shield third fold 1600, including the forehead band top securing tabs 1601, on top of the inside top panels 1602, that pivots along the inside top panel folding lines 1603, and inserted into the left top forehead band attachment slot 1604a, and the right top forehead band attachment slot 1604b, (not shown), respectively, cut into the flexible transparent face plate 1605, as you push the diagonal panels 1606, that pivots along the diagonal panels folding lines 1607, toward the forehead rest back panel 1608, that pivots along the forehead rest back panel folding lines 1609. FIG. 16 shows a perspective view of the Origami One Piece Duo-Face Shield third fold 1600, including the bottom panels 1610, that pivots along the bottom panels folding lines 1611, as the forehead band bottom securing tabs 1612, are inserted into the left bottom forehead band attachment slot 1613a, and the right bottom forehead band attachment slot 1613b, respectively, cut into the flexible transparent face plate 1605, as the inside top panels 1602, angles parallel to the top panels 1614, that pivots along the top panel folding lines 1615.

Figure 17:
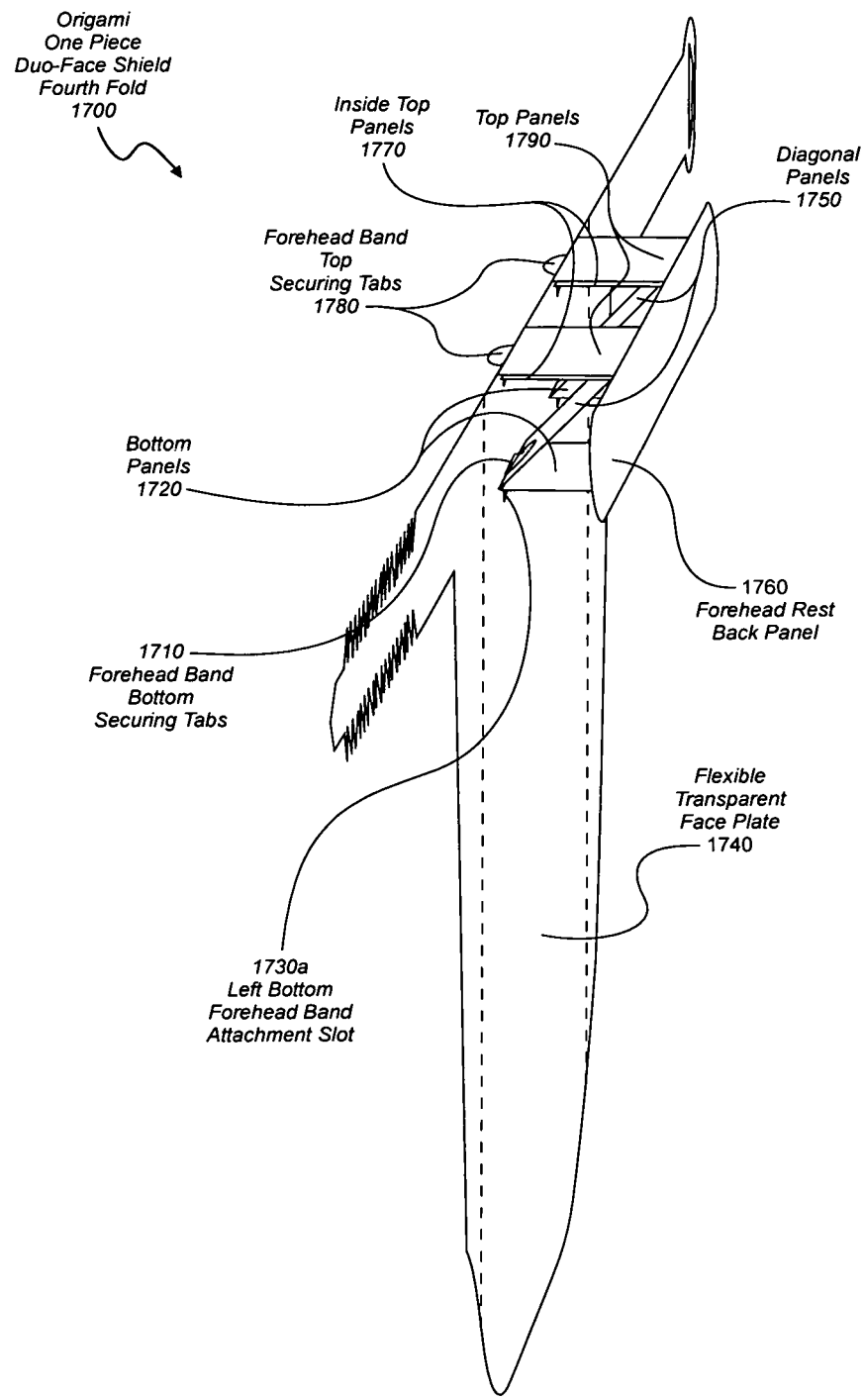
FIG. 17 illustrates a perspective view of the fourth fold of the Origami One Piece Duo-Face Shield to create the forehead band component of the face shield for an embodiment of the origami one piece face shield.

FIG. 17 illustrates a perspective view of the Origami One Piece Duo-Face Shield fourth fold 1700. FIG. 17 shows a perspective view of the Origami One Piece Duo-Face Shield fourth fold 1700, including the forehead band bottom securing tabs 1710, on top of the bottom panels 1720, inserted through the left bottom forehead band attachment slot 1730a, and the right top forehead band attachment slot 1730b, (not shown), cut into the flexible transparent face plate 1740, angling the diagonal panels 1750, toward the top of the forehead rest back panel 1760, and positioning the inside top panels 1770, with its forehead band top securing tabs 1780, parallel to the top panels 1790, for increased strength and rigidity of the Forehead rest back panel 1760, that rests along the user's forehead, creating a gap between the flexible transparent face plate 1740, and the user's head, for ventilation.

Figure 18:
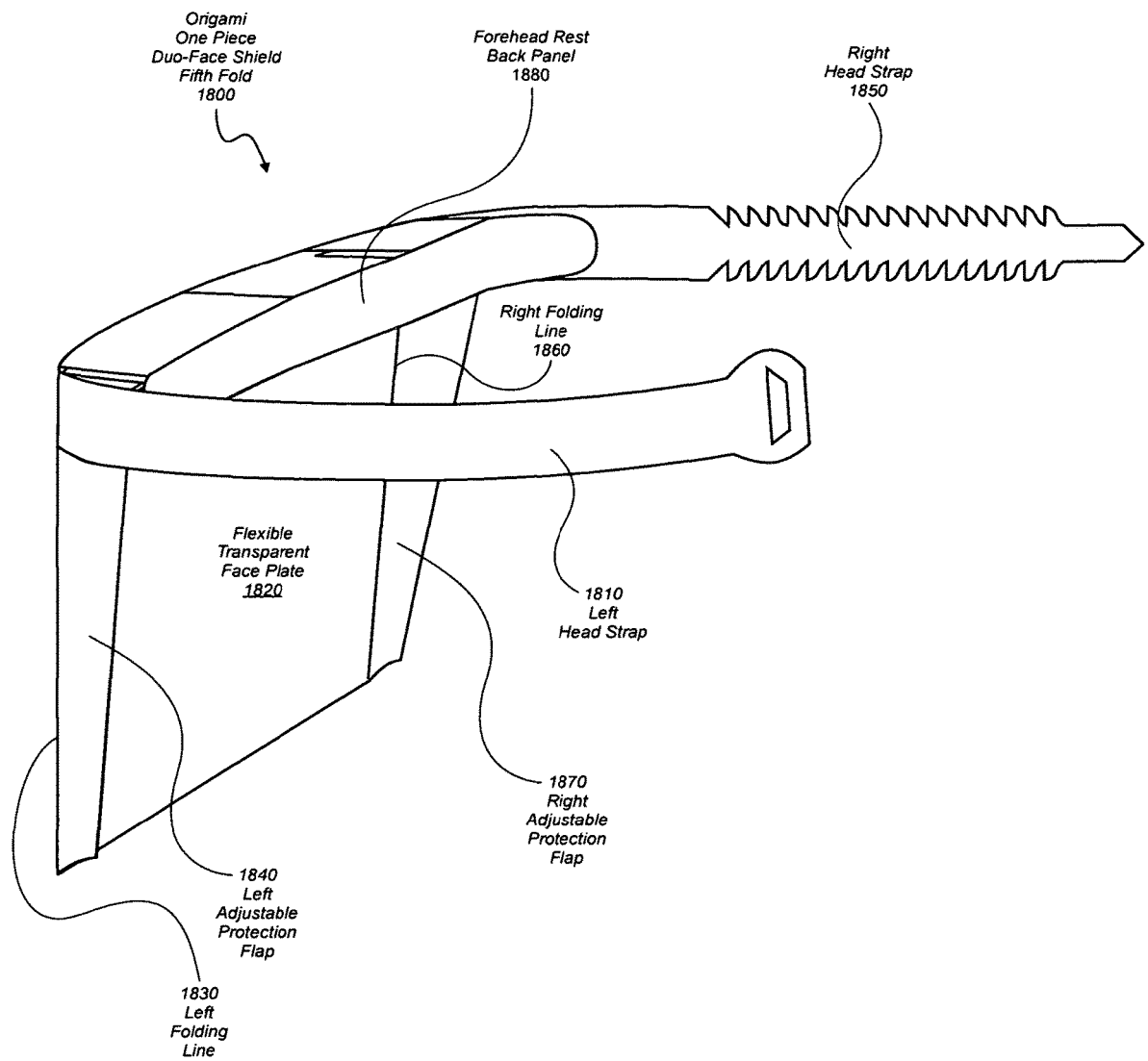
FIG. 18 illustrates a perspective view of the fifth fold of the Origami One Piece Duo-Face Shield to create the head strap component of the face shield for an embodiment of the origami one piece face shield.

FIG. 18 illustrates a perspective view of the Origami One Piece Duo-Face Shield fifth fold 1800. FIG. 18 shows a perspective view of the Origami One Piece Duo-Face Shield fifth fold 1800, including folding the left head strap 1810, connected to the flexible transparent face plate 1820, pivoting along the left folding line 1830, of the left adjustable protection flap 1840, to a perpendicular position relative to the flexible transparent face plate 1820, vertical plane. FIG. 18 shows a perspective view of the right head strap 1850, connected to the flexible transparent face plate 1820, pivoting along the right folding line 1860, of the right adjustable protection flap 1870, to a perpendicular position relative to the flexible transparent face plate 1820, vertical plane. FIG. 18 shows a perspective view of the left head strap 1810, the right head strap 1850, and the forehead rest back panel 1880, forming the frontal circumference of the head strap component (see FIG. 11, head strap components 1110).

Figure 19:
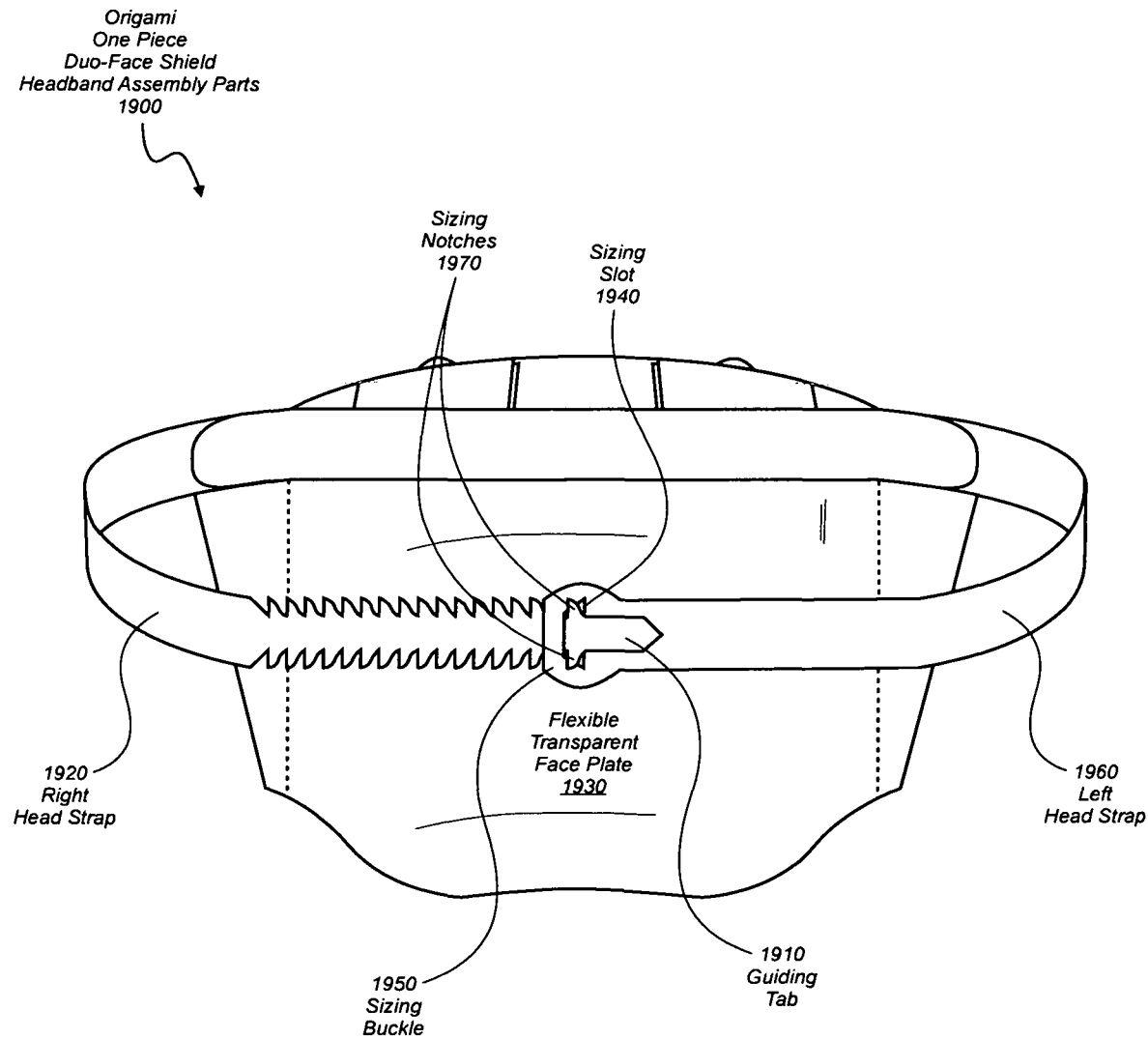
FIG. 19 illustrates a perspective view for an embodiment of the Origami One Piece Duo-Face Shield headband assembly parts for an embodiment of the origami one piece face shield.

FIG. 19 illustrates a perspective view of the Origami One Piece Duo-Face Shield headband assembly parts 1900. FIG. 19 shows a perspective view of the Origami One Piece Duo-Face Shield headband assembly parts 1900, including the guiding tab 1910, of the right head strap 1920, connected to the flexible transparent face plate 1930, inserted into the sizing slot 1940, of the sizing buckle 1950, of the left head strap 1960, until it reaches and locks the sizing notches 1970, forming the basic head band component (see FIG. 11, head strap components 1110), of the face shield.

See FIG. 9 Origami One Piece X-Face Shield headband sizing system 900.

Figure 20:
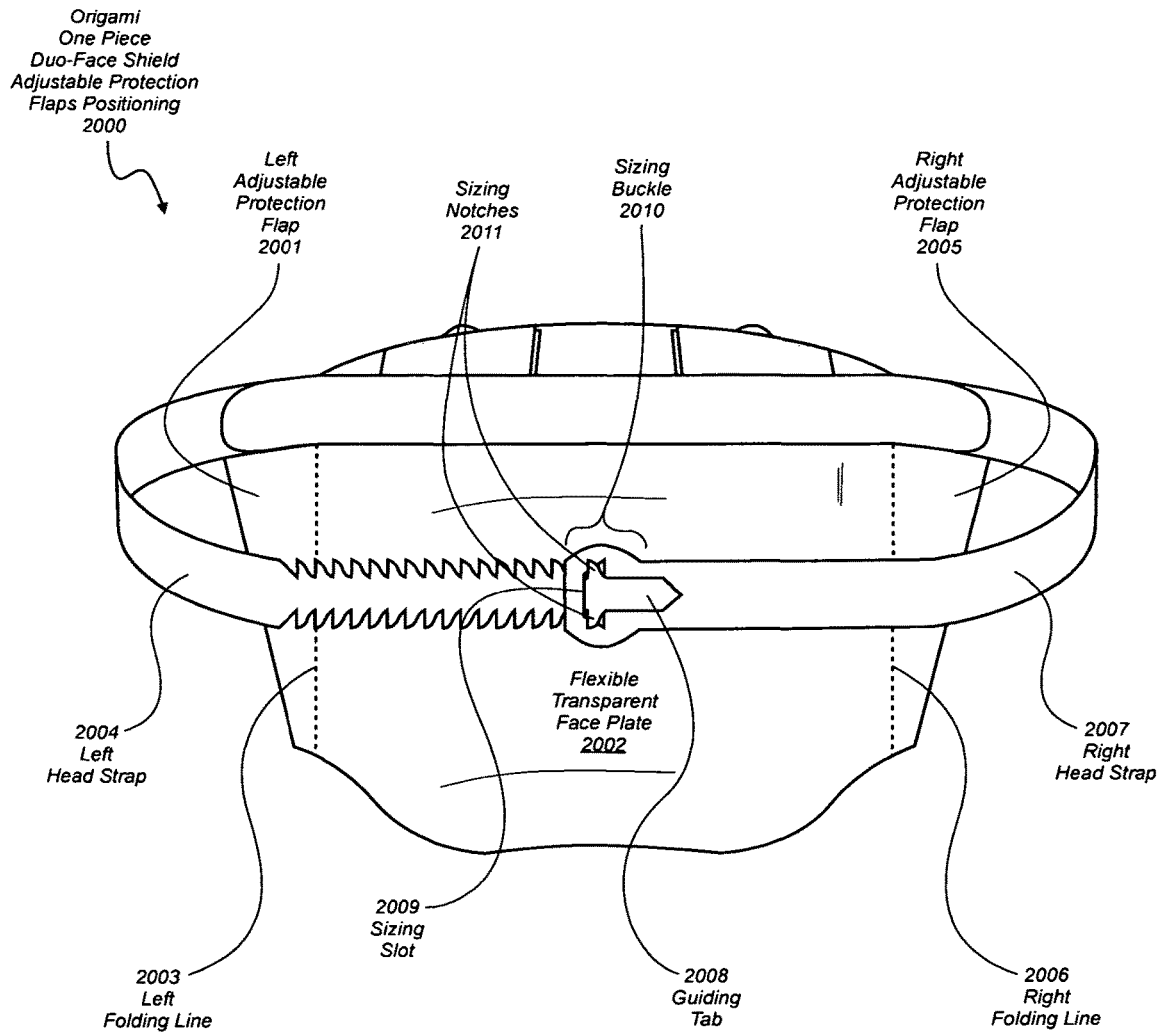
FIG. 20 illustrates a perspective view for an embodiment of the Origami One Piece Duo-Face Shield adjustable protection flaps positioning for an embodiment of the origami one piece face shield.

FIG. 20 illustrates a perspective view of the Origami One Piece Duo-Face Shield adjustable protection flaps positioning 2000. FIG. 20 shows a perspective view of the Origami One Piece Duo-Face Shield adjustable protection flaps positioning 2000, including folding the left adjustable protection flap 2001, connected to the flexible transparent face plate 2002, along the left folding line 2003, as it pivots with the left head strap 2004, to an angled position relative to the flexible transparent face plate 2002, vertical plane. FIG. 20 shows a perspective view of the right adjustable protection flap 2005, connected to the flexible transparent face plate 2002, along the right folding line 2006, as it pivots with the right head strap 2007, to an angled position relative to the flexible transparent face plate 2002, vertical plane. FIG. 20 shows a perspective view of the guiding tab 2008, of the left head strap 2004, as it is inserted into the sizing slot 2009, of the sizing buckle 2010, of the right head strap 2007, until the sizing notches 2011, locks into place, according to the user's head size.

Figure 21:
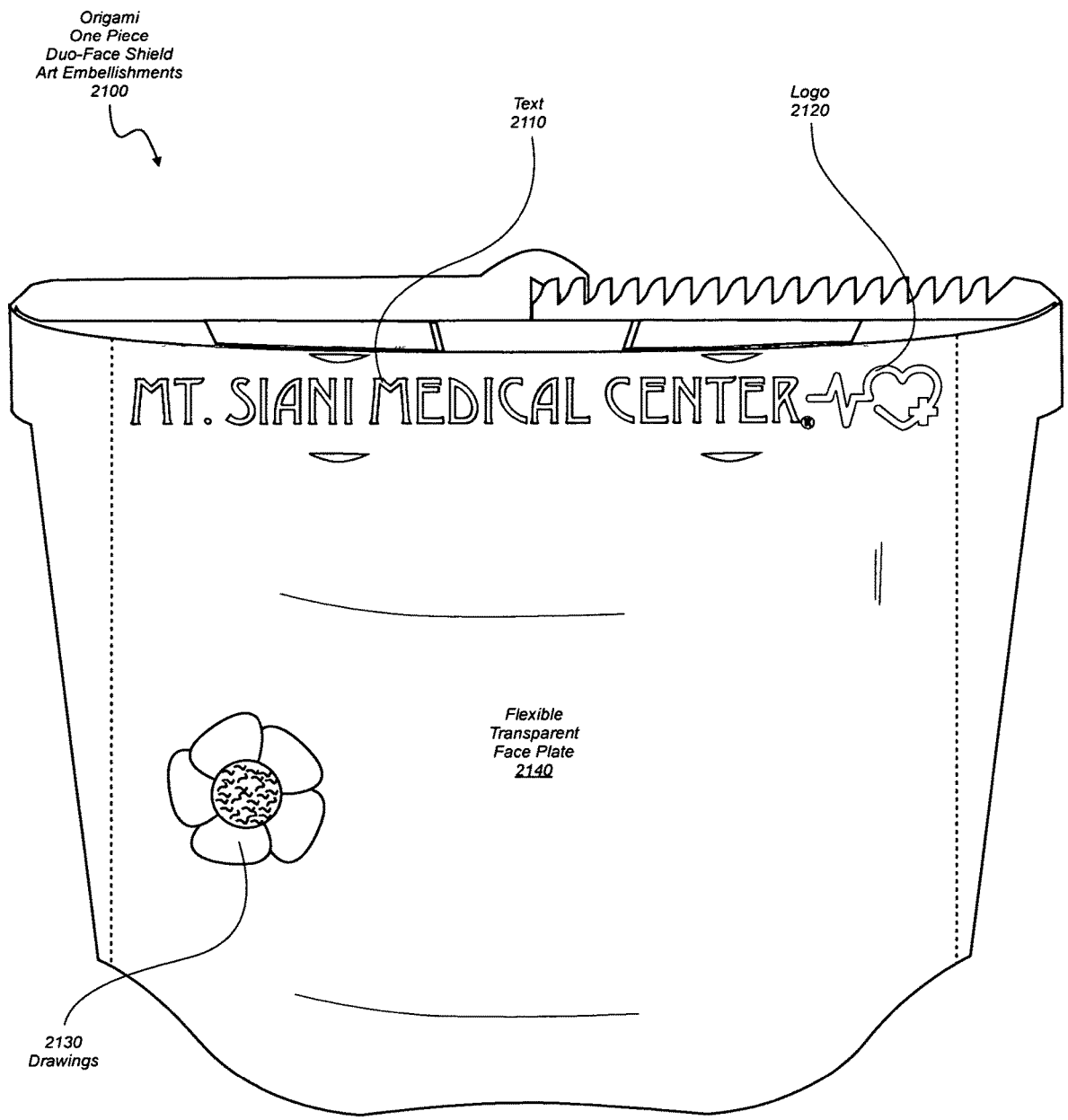
FIG. 21 illustrates a perspective view for an embodiment of the Origami One Piece Duo-Face Shield art embellishment for an embodiment of the origami one piece face shield.

FIG. 21 illustrates a perspective view of the Origami One Piece Duo-Face Shield art embellishments 2100. FIG. 21 shows a perspective view of the Origami One Piece Duo-Face Shield art embellishments 2100, including but not limited, to a plurality of Text 2110, Logos 2120, and drawings 2130, within the flexible transparent face plate 2140, and/or any other surfaces of the Origami One Piece Face Shield embodiments components.

Figure 22:
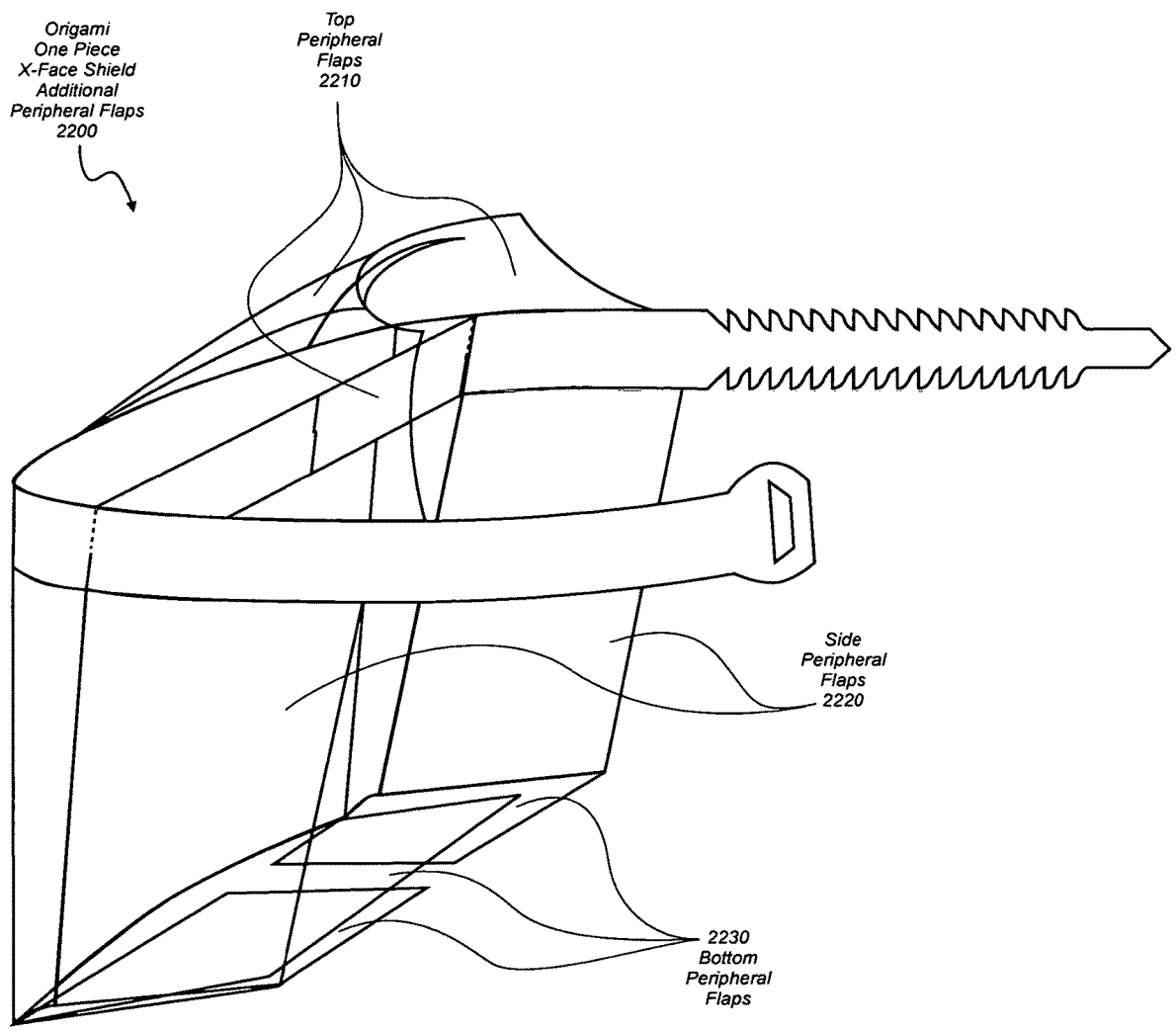
FIG. 22 illustrates a perspective view for an embodiment of the Origami One Piece X-Face Shield additional peripheral flaps for an embodiment of the origami one piece face shield.

FIG. 22 illustrates a perspective view of the Origami One Piece X-Face Shield additional peripheral flaps 2200. FIG. 22 shows a perspective view of the Origami One Piece X-Face Shield additional peripheral flaps 2200, including, but not limited, to the top peripheral flaps 2210, the side peripheral flaps, and the bottom peripheral flaps, where all flaps are part of the Origami One Piece Face Shield.

What is claimed as invention is:

1. A self-contained, one piece, contiguous, lightweight, disposable, ventilated, face shield apparatus configured for the protection of regions of thin and penetrable membranes, such as the eyes, nose and mouth of medical personnel, essential workers and the general public from exposure to infectious, and/or hazardous pathogens carrying fluids and particulate materials such as the Coronaviridae family of viruses including COVID-19, said face shield apparatus comprising:

a waterproof, flexible, transparent, face plate component, configured to cover a user's eyes, nose and mouth regions;

a forehead band component, configured to rest against said user's forehead and is connected, and separates, said face plate component, from the user's face, to allow for ventilation and the use of eyeglasses and/or face masks, by the user, wherein the forehead band component is adapted from a left forehead band of said forehead band component, and a right forehead band of said forehead band component, crossing each other as they interconnect and are locked by a plurality of slits along its length, with a resulting combined total length of the forehead band component being shorter than a total length of said face plate component, bending the face shield apparatus into an arcuate angle for ventilation and the use of eyeglasses and/or face masks;

a head strap component, connected to said face plate component, and/or said forehead band component, said head strap component adapted to wrap around the user's head to hold said face shield apparatus in place, the head strap component comprising of:

a head strap sizing component, connected to said head strap component, and adapted to size said head strap component, to the user's head size, said head strap sizing component comprising of:

a sizing slot within a sizing buckle on a first part of said head strap component;

a plurality of sizing notches on a second part of said head strap component, the plurality of sizing notches being configured to be guided through said sizing slot within said sizing buckle on the first part of said head strap component and slid in until a diameter of said head strap component achieves security around the user's head;

a plurality of adjustable protection flaps, connected to said face plate component, and/or said forehead band component, and/or said head strap component, the plurality of adjustable protection flaps being configured to further protect the user's eyes, nose, and mouth from contaminants approaching the face from arcuate angles, creating an expanded region of protection; and wherein the face shield apparatus is made from a single, contiguous, transparent/semi-transparent, flexible, piece of material.

2. The face shield device of claim 1, wherein the head strap component is adapted from a plurality of flexible bands formed from the same single, contiguous, transparent/semi-transparent, flexible, piece of material.

3. The face shield device of claim 1, wherein the head strap sizing component comprises:

(a) a left head band ending, the left head band ending being rounded and having the sizing buckle that contains sizing slot, wherein top and bottom edges of the left head band ending are slanted at an angle from a shorter length outward edge to a longer length inner edge so as to permit entrance of the sizing notches but to restrict and secure them when pulled in the reversed direction;

(b) a right head band ending, the right head band ending having the plurality of sizing notches on respective upper and lower edges, generally right triangular in form, with the hypotenuse facing an end of said right head band end and a pointed guiding tab to facilitate entry into the sizing slot of the sizing buckle of said left head band ending.

4. The face shield device of claim 1, wherein the plurality of adjustable protection flaps, connected to said face plate component, and/or said forehead band component, and/or said head strap component, are configured to further protect the user's eyes, nose, and mouth from contaminants approaching the face from arcuate angles, creating the expanded region of protection and therefore an enhanced defense against contagion.

5. The face shield device of claim 1, wherein said single, contiguous, transparent/semi-transparent, flexible, piece of material is composed of a material is selected from the group consisting of polyvinyl chloride, polystyrene, acrylic, acetate, polyethylene, terephthalate, polystyrene, polycarbonate, polyester, polyolefin, polyurethane, acrylic, acetate, PVC, PET, PETG, OPS, Polycarbonate and APET film.

6. The face shield device of claim 1, wherein said single, contiguous, transparent/semi-transparent, flexible, piece of material naturally possesses or is chemically treated to provide optical effects or protections such as anti-fogging, ultraviolet light, glare, radiation, blue light, tint, and opacity.

7. The face shield device of claim 1, wherein said single, contiguous, transparent/semi-transparent, flexible, piece of material includes a plurality of indicia comprising texts, logos, drawings, advertisings, sizing information, and general instructions.

8. The method of claim 1, wherein said single, contiguous, transparent/semi-transparent, flexible, piece of material being adapted for flat storage, package and shipping when in its unfolded planar configuration.

9. The method of claim 1, wherein a plurality of said single, contiguous, transparent/semi-transparent, flexible, pieces of material can be stacked, packaged, and stored for handing and shipping.

10. A self-contained, one piece, contiguous, lightweight, disposable, ventilated, face shield apparatus configured for the protection of regions of thin and penetrable membranes, such as the eyes, nose and mouth of medical personnel, essential workers and the general public from exposure to infectious, and/or hazardous pathogens carrying fluids and particulate materials such as the Coronaviridae family of viruses including COVID-19, said face shield apparatus comprising:

a waterproof, flexible, transparent, face plate component, configured to cover a user's eyes, nose and mouth regions;

a forehead band component, configured to rest against said user's forehead and is connected, and separates, said face plate component, from the user's face, to allow for ventilation and the use of eyeglasses and/or face masks, by the user, wherein the forehead band component is adapted from a plurality of interconnected, foldable panels, securing tabs and attachment slots, said interconnected, foldable panels, securing tabs, and attachment slots, when folded and secured in the proper sequence, create the forehead band component configured to rest against the user's forehead;

a head strap component, connected to said face plate component, and/or said forehead band component, said head strap component adapted to wrap around the user's head to hold said face shield apparatus in place, the head strap component comprising of:

a head strap sizing component, connected to said head strap component, and adapted to size said head strap component, to the user's head size, said head strap sizing component comprising of:

a sizing slot within a sizing buckle on a first part of said head strap component;

a plurality of sizing notches on a second part of said head strap component, the plurality of sizing notches being configured to be guided through said sizing slot within said sizing buckle on the first part of said head strap component and slid in until a diameter of said head strap component achieves security around the user's head;

a plurality of adjustable protection flaps, connected to said face plate component, and/or said forehead band component, and/or said head strap component, the plurality of adjustable protection flaps being configured to further protect the user's eyes, nose, and mouth from contaminants approaching the face from arcuate angles, creating an expanded region of protection; and wherein the face shield apparatus is made from a single, contiguous, transparent/semi-transparent, flexible, piece of material.

11. The face shield device of claim 10, wherein the head strap component is adapted from a plurality of flexible bands formed from the same single, contiguous, transparent/semi-transparent, flexible, piece of material.

12. The face shield device of claim 10, wherein the head strap sizing component comprises:
  (a) a left head band ending, the left head band ending being rounded and having the sizing buckle that contains sizing slot, wherein top and bottom edges of the left head band ending are slanted at an angle from a shorter length outward edge to a longer length inner edge so as to permit entrance of the sizing notches but to restrict and secure them when pulled in the reversed direction;
  (b) a right head band ending, the right head band ending having the plurality of sizing notches on respective upper and lower edges, generally right triangular in form, with the hypotenuse facing an end of said right head band end and a pointed guiding tab to facilitate entry into the sizing slot of the sizing buckle of said left head band ending.

13. The face shield device of claim 10, wherein the plurality of adjustable protection flaps, connected to said face plate component, and/or said forehead band component, and/or said head strap component, are configured to further protect the user's eyes, nose, and mouth from contaminants approaching the face from arcuate angles, creating the expanded region of protection and therefore an enhanced defense against contagion.

14. The face shield device of claim 10, wherein said single, contiguous, transparent/semi-transparent, flexible, piece of material is composed of a material is selected from the group consisting of polyvinyl chloride, polystyrene, acrylic, acetate, polyethylene, terephthalate, polystyrene, polycarbonate, polyester, polyolefin, polyurethane, acrylic, acetate, PVC, PET, PETG, OPS, Polycarbonate and APET film.

15. The face shield device of claim 10, wherein said single, contiguous, transparent/semi-transparent, flexible, piece of material naturally possesses or is chemically treated to provide optical effects or protections such as anti-fogging, ultraviolet light, glare, radiation, blue light, tint, and opacity.

16. The face shield device of claim 10, wherein said single, contiguous, transparent/semi-transparent, flexible, piece of material includes a plurality of indicia comprising texts, logos, drawings, advertisings, sizing information, and general instructions.

17. The method of claim 10, wherein said single, contiguous, transparent/semi-transparent, flexible, piece of material is adapted for flat storage, package and shipping when in its unfolded planar configuration.

18. The method of claim 10, wherein a plurality of said single, contiguous, transparent/semi-transparent, flexible, pieces of material can be stacked, packaged, and stored for handing and shipping.

\* \* \* \* \*